United States Patent
Liebeskind et al.

(10) Patent No.: US 11,471,868 B2
(45) Date of Patent: Oct. 18, 2022

(54) REDOX DEHYDRATION COUPLING CATALYSTS AND METHODS RELATED THERETO

(71) Applicant: Emory University, Atlanta, GA (US)

(72) Inventors: Lanny Steven Liebeskind, Atlanta, GA (US); Pavan Kumar Reddy Gangireddy, Stone Mountain, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 17/067,386

(22) Filed: Oct. 9, 2020

(65) Prior Publication Data

US 2021/0053044 A1    Feb. 25, 2021

Related U.S. Application Data

(62) Division of application No. 15/769,634, filed as application No. PCT/US2016/057618 on Oct. 19, 2016, now abandoned.

(Continued)

(51) Int. Cl.
*C07C 231/02* (2006.01)
*B01J 31/26* (2006.01)
(Continued)

(52) U.S. Cl.
CPC ............ *B01J 31/26* (2013.01); *B01J 27/122* (2013.01); *B01J 31/0218* (2013.01); *B01J 31/0271* (2013.01); *B01J 31/181* (2013.01); *B01J 31/2269* (2013.01); *C07C 231/02* (2013.01); *C07D 275/04* (2013.01); *C07D 293/06* (2013.01); *C07D 293/12* (2013.01); *B01J 2231/4283* (2013.01); *B01J 2231/64* (2013.01); *B01J 2531/16* (2013.01)

(58) Field of Classification Search
CPC ...... B01J 31/26; B01J 27/122; B01J 31/0218; B01J 31/0271; B01J 31/181; B01J 31/2269; B01J 2231/4283; B01J 31/0247; B01J 2531/16; B01J 31/0272; B01J 31/0275; C07C 231/02; C07D 275/04; C07D 293/06; C07D 293/12
USPC .......................................................... 564/139
See application file for complete search history.

(56) References Cited

U.S. PATENT DOCUMENTS 4,350,702 A     9/1982  Baggaley
8,921,599 B2   12/2014  Liebeskind
(Continued)

FOREIGN PATENT DOCUMENTS

WO    2015054337    4/2015

OTHER PUBLICATIONS

Akondi et al. Aerobic, Diselenide-Catalyzed Redox Dehydration: Amides and Peptides, Org. Lett. 2018, 20, 538-541.
(Continued)

*Primary Examiner* — Taylor V Oh
(74) *Attorney, Agent, or Firm* — Emory Patent Group

(57) ABSTRACT

This disclosure relates to synthetic coupling methods using catalytic molecules. In certain embodiments, the catalytic molecules comprise heterocyclic thiolamide, S-acylthiosalicylamide, disulfide, selenium containing heterocycle, diselenide compound, ditelluride compound or tellurium containing heterocycle. Catalytic molecules disclosed herein are useful as catalysts in the transformation of hydroxy group containing compounds to amides, esters, ketones, and other carbon to heteroatom or carbon to carbon transformations

2 Claims, 18 Drawing Sheets

Related U.S. Application Data

(60) Provisional application No. 62/378,785, filed on Aug. 24, 2016, provisional application No. 62/243,353, filed on Oct. 19, 2015.

(51) Int. Cl.

| | | |
|---|---|---|
| *C07D 275/04* | (2006.01) | |
| *C07D 293/12* | (2006.01) | |
| *C07D 293/06* | (2006.01) | |
| *B01J 31/02* | (2006.01) | |
| *B01J 31/18* | (2006.01) | |
| *B01J 27/122* | (2006.01) | |
| *B01J 31/22* | (2006.01) | |

(56) References Cited

U.S. PATENT DOCUMENTS

| | | |
|---|---|---|
| 9,700,881 B2 | 7/2017 | Liebeskind |
| 2016/0243534 A1 | 8/2016 | Liebeskind |

OTHER PUBLICATIONS

Beletskaya et al. Copper in cross-coupling reactions the post-Ullmann chemistry, Coordination Chemistry Reviews 248 (2004) 2337-2364.

Bhakuni et al. An efficient copper mediated synthetic methodology for benzo[d]isothiazol-3(2H)-ones and related sulfur-nitrogen heterocycles, Tetrahedron Letters 53 (2012) 1354-1357.

But et al. The Mitsunobu Reaction: Origin, Mechanism, Improvements, and Applications, Chem. Asian J. 2007, 2, 1340-1355.

Chen et al. Cu(II)-Mediated C-S/N-S Bond Formation via C-H Activation: Access to Benzoisothiazolones Using Elemental Sulfur, Org. Lett. 2014, 16, 5644-5647.

Ghosh et al. Copper-Catalyzed Oxidative Amidation of Aldehydes with Amine Salts: Synthesis of Primary, Secondary, and Tertiary Amides, J. Org. Chem. 2012, 77, 8007-8015.

Henke et al. Thioimides: New Reagents for Effective Synthesis of Thiolesters from Carboxylic Acids, J. Org. Chem. 2008, 73, 7783-7784.

Jiang et al. Copper-catalyzed C—N bond formation through C—H/N—H activation: a novel approach to the synthesis of multisubstituted ureas, Chem. Commun., 2013, 49, 819.

Liebeskind et al. A Copper-Catalyzed, pH-Neutral Construction of High-Enantiopurity Peptidyl Ketones from Peptidic S-Acylthiosalicylamides in Air at Room Temperature, Angew. Chem. Int. Ed. 2009, 48, 1417-1421.

Liebeskind et al. Benzoisothiazolone Organo/Copper-Cocatalyzed Redox Dehydrative Construction of Amides and Peptides from Carboxylic Acids using (EtO)3P as the Reductant and O2 in Air as the Terminal Oxidant, J. Am. Chem. Soc. 2016, 138, 6715-6718.

Lundberg et al. Catalytic amide formation from non-activated carboxylic acids and amines, Chem. Soc. Rev., 2014, 43, 2714.

Mukaiyama, Oxidation-Reduction Condensation, Angew. Chem. Int. Ed. Engl. vol. 15 (1976) No. 2, 94-103.

O'Brien et al. Breaking the Ring through a Room Temperature Catalytic Wittig Reaction, Chem. Eur. J. 2013, 19, 5854-5858.

Pubchem, 2-(alpha,alpha-Dimethylbenzyl)-1,2-benzisothiazole-3(2H)-one, availble at https://pubchem.ncbi.nlm.nih.gov/compound/2-_2-Phenylpropan-2-yl_-1.../compound/9835147.

Pubchem, 2-[2-(Dimethylamino)ethyl]-5-nitro-1,2-benzothiazol-3-one, available at https://pubchem.ncbi.nlm.nih.gov/compound/20030236.

Pubchem, 5-Methyl-2-[1-(4-methyl-1,3-thiazol-2-yl)ethyl]-1,2-benzothiazol-3-one . . . . https://pubchem.ncbi.nlm.nih.gov/compound/20524321.

Raab et al. Ligand effects in the copper catalyzed aerobic oxidative carbonylation of methanol to dimethyl carbonate (DMC), Journal of Molecular Catalysis A: Chemical 175 (2001) 51-63.

Rossi et al. Selective Formation of Secondary Amides via the Copper-Catalyzed Cross-Coupling of Alkylboronic Acids with Primary Amides, Org. Lett., 2013,15 (9), pp. 2314-2317.

Rao et al. Copper(II)-Catalyzed Direct Sulfonylation of C(sp2)-H Bonds with Sodium Sulfinates, Org. Lett. 2015, 17, 2784-2787.

Varela et al. Mechanistic Insights into the Aerobic Cu(I)-Catalyzed Cross-Coupling of S-Acyl Thiosalicylamide Thiol Esters and Boronic Acids, Organometallics. 2012, 31(22): 7958-7968.

Veliz et al. Mitsunobu reactions of nucleoside analogs using triisopropyl phosphite-DIAD, Tetrahedron Letters 47 (2006) 3153-3156.

Wang et al. Copper-Catalyzed Intramolecular N—S Bond Fomnation by Oxidative Dehydrogenative Cyclization, J. Org. Chem. 2013, 78, 7337-7342.

Zhang et al. Mobilizing Cu(I) for Carbon-Carbon Bond Forming Catalysis in the Presence of Thiolate. Chemical Mimicking of Metallothioneins, J Am Chem Soc. 2011, 133(16): 6403-6410.

| | product | # | % (t, h) |
|---|---|---|---|
| 1 | Cbz-L-Trp-Phe-OMe | 3a | 89 (18)<br>91 (24)ᶜ |
| 2 | Cbz-L-Phe-NHcyclopropyl | 3b | 79 (10) |
| 3 | 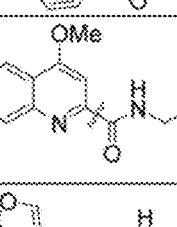 | 3c | 68 (18) |
| 4 | 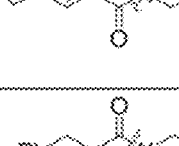 | 3d | 71 (36)ᵉ |
| 5 | 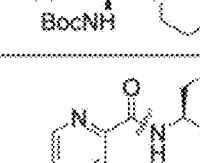 | 3e | 72 (18) |
| 6 | 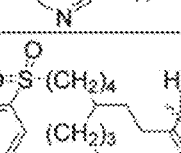 | 3f | 83 (18) |
| 7 | 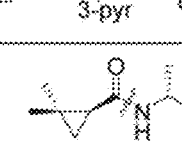 | 3g | 78 (36)ᵉ |
| 8 | 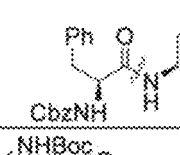 | 3h | 82 (36) |
| 9 | 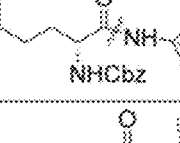 | 3i | 78 (24) |
| 10 | 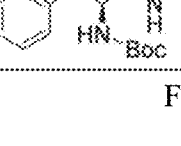 | 3j | 77 (24)ᶜ |
| 11 |  | 3k | 79 (24) |
| 12 |  | 3l | 61 (36) |
FIG. 1D

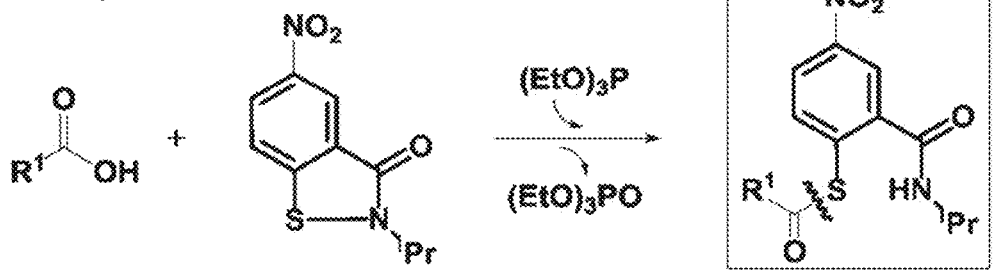
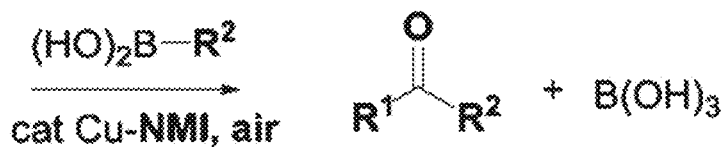
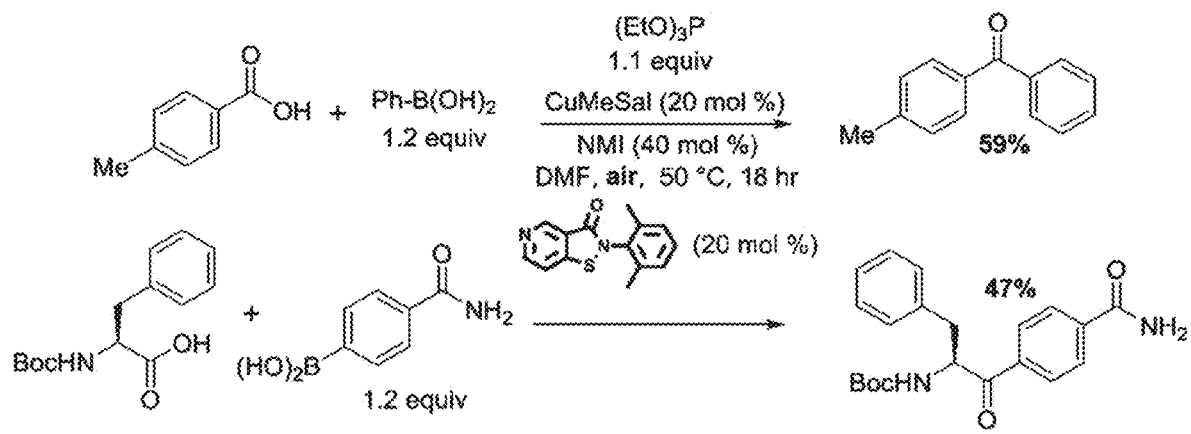
FIG. 4

| S.No | Cu catalyst | Temperature | Time (yield) |
|---|---|---|---|
| 1 | Cu(NMI)₄I₂ (10 mol%) | 55 °C | 3h (85%) |
| 2 | Cu(NMI)₄I₂ (10 mol%) | RT | 30h (81%) |
| 3 | --- | 55 °C | 24h (65%) |
| 4 | CuI (10 mol%) | 55 °C | 5h (77%) |

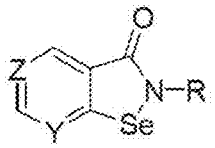
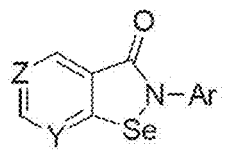

2a: Z = Y = CH, R = H
2b: Z = Y = CH, R = COPh
2c: Z = CNO$_2$, Y = CH, R = $^i$Pr
2d: Z = CNO$_2$, Y = CH, R = adamantyl
2e: Z = CNO$_2$, Y = CH, R = C(Me)$_2$Ph
2f: Z = Y = CH, R = C(Me)$_2$2-pyridyl
2g: Z = CNO$_2$, Y = CH, R = C(Me)$_2$2-pyridyl
2h: Z = COMe, Y = CH, R = C(Me)$_2$2-pyridyl
2i: Z = CNO$_2$, Y = CH, R = CH$_2$CH$_2$NMe$_2$
2j: Z = CNO$_2$, Y = CH, R = CH$_2$CH$_2$CH$_2$NMe$_2$ 2k: Z = Y = CH, Ar = 2-pyridyl
2l: Z = CNO$_2$, Y = CH, Ar = 2-pyridyl
2m: Z = Y = CH, Ar = 4-pyridyl
2n: Z = CNO$_2$, Y = CH, Ar = 2-(2-pyridyl)phenyl

FIG. 14

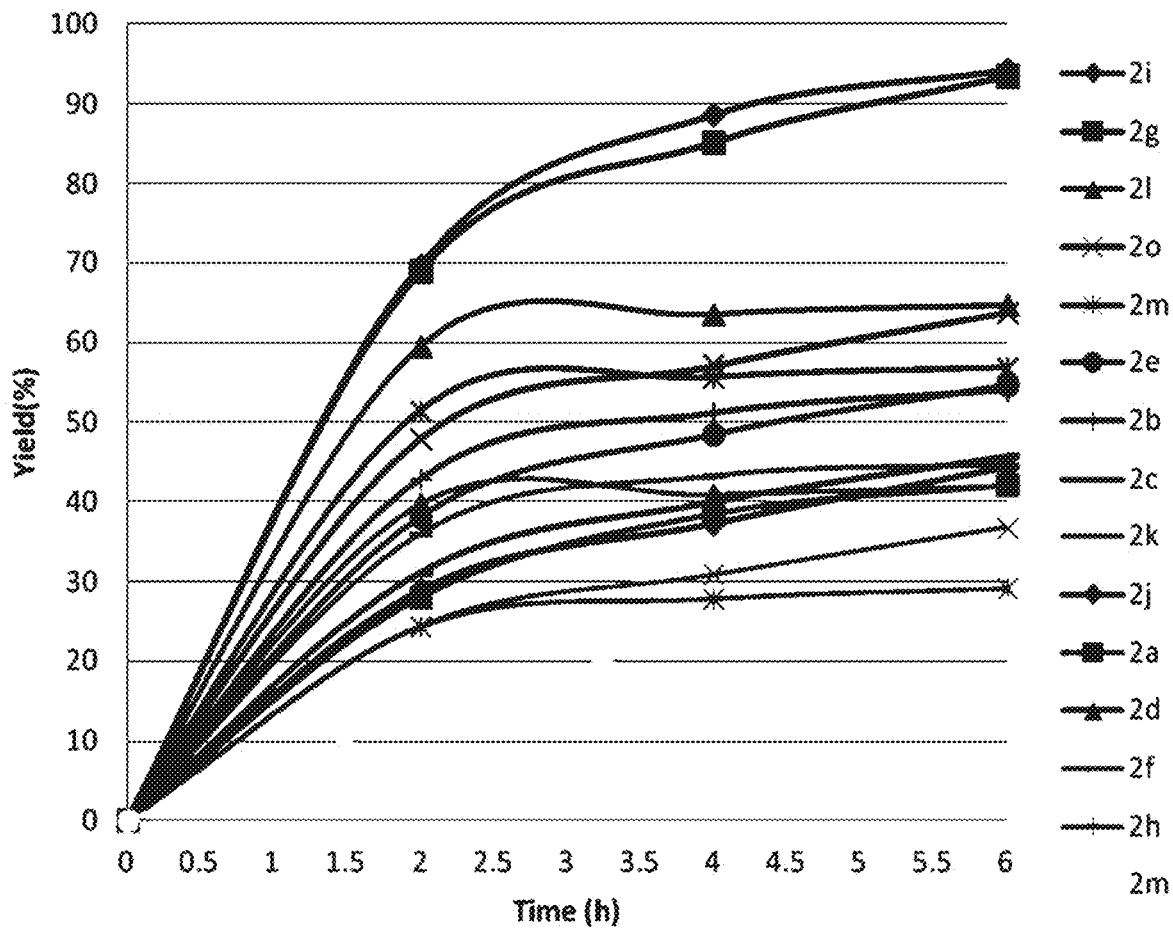

FIG. 15

REDOX DEHYDRATION COUPLING CATALYSTS AND METHODS RELATED THERETO

CROSS-REFERENCE TO RELATED APPLICATIONS

This application is a division of U.S. application Ser. No. 15/769,634 filed Apr. 19, 2018, which is the National Stage of International Application No. PCT/US2016/057618 filed Oct. 19, 2016, which claims priority to U.S. Provisional Application No. 62/243,353 filed Oct. 19, 2015 and U.S. Provisional Application No. 62/378,785 filed Aug. 24, 2016. The entirety of each of these applications is hereby incorporated by reference for all purposes

STATEMENT REGARDING FEDERALLY FUNDED RESEARCH

This invention was made with government support under CHE-1362281 awarded by the National Science Foundation. The government has certain rights in the invention.

BACKGROUND

Amide bonds are key component in many biological materials and known drugs. For example, Atorvastatin, which blocks the production of cholesterol, and Valsartan, a blockade of angiotensin-II receptors, both contain amide bonds. Amide bonds also form the basis of many important materials, polymers, and diagnostics. Mild, efficient and general methods for the construction of amide and peptide linkages are desired for the production of therapeutics, biological materials, advanced materials, and biological tools that are based upon amide, peptide, protein, and glycopeptides motifs.

Amide bonds are typically synthesized from the union of carboxylic acids and amines; however, the reaction between these two functional groups is not spontaneous at ambient temperature, with the elimination of water only taking place at extremely high temperatures (>200 C), conditions which are typically detrimental to the integrity of the reacting compounds themselves.

Some coupling methods used to generate amide bonds from carboxylic acids and amines utilize special activating protocols or the construction of special functionalities such as azides and ketoacids or hydroxylamines. There are a number of 'coupling reagents' which convert the hydroxy (—OH) of the carboxylic acid to a good leaving group prior to the treatment with the amine. Classical reagents include carbodiimides, phosphonium salts, uronium salts and reagents generating acid halides.

Generating amine reactive acid halides, using reagents such as thionyl chloride and phosphorus pentachloride, is not compatible with many synthetic strategies, due to the formation of hydrochloric acid. Newer reagents used to generate acid halides such as Deoxo-Fluor and DAST are expensive, hazardous, and require purification by chromatography after the reaction.

Carbodiimides such as dicyclohexylcarbodiimide (DCC) are commonly used as coupling reagents; however, these reagents need to be used in conjunction with additives such as 1-hydroxy-H-benzotriazole (HOBt) or 1-hydroxy-7-azabenzotriazole (HOAt) in order to decrease undesired epimerization that can occur when using chiral amino acids. These additives yield by-products that catalyze the 'dimerization' of DCC. In addition to this, safety considerations have to be carefully considered when using benzotriazoles (or variants thereof) because of their explosive properties.

The coupling reagents based on the HOBt/HOAt system, such as uronium/aminium salts like HATU react with the carboxylic acids to form active esters; however, side reactions of the coupling reagents with the amines lead to the formation of guanidinium side products. The phosphonium salts, which are also based on HOBt/HOAt, such as BOP are undesirable due to the carcinogenic and respiratory toxicity associated with HMPA generated in the reaction.

More recent approaches to amide bond formation include Staudinger ligation, a modification of the Staudinger reaction which produces an amide linked product from the reaction of a modified triarylphosphine and azides, as well as the further modified version which involves the reaction of thioacids with azides.

Another method is the 'native chemical ligation' method which is used for the preparation of proteins. It involves the reaction between a peptide alpha-thioester and a cysteine-peptide, to yield a product with a native amide bond at the ligation site. However, the thioalkyl esters are rather unreactive and despite the use of a catalyst the reaction typically takes 24-28 hours.

Although the above methodologies have been applied to the synthesis of proteins and protein analogues, there is a continued interest in the wider application of the tools of organic chemistry to the study of proteins. Despite the number of coupling reagents that have been reported, most reagents are simply not efficient for a broad range of amide bond forming reactions. Thus, there remains a need for simple, effective reagents with high conversions and low levels of epimerization of chiral compounds that produces limited by-products.

Liebeskind et al. report benzoisothiazolone organo/copper-cocatalyzed redox dehydrative construction of amides and peptides from carboxylic acids using $(EtO)_3P$ as the reductant and $O_2$ in air as the terminal oxidant. J. Am. Chem. Soc., 2016, 138 (21), pp 6715-6718. See also WO/2015/054337.

References cited herein are not an admission of prior art.

SUMMARY

This disclosure relates to synthetic coupling methods using catalytic molecules. In certain embodiments, the catalytic molecules comprise heterocyclic thiolamide, S-acylthiosalicylamide, disulfide, selenium containing heterocycle, diselenide compound, ditelluride compound or tellurium containing heterocycle. Catalytic molecules disclosed herein are useful as catalysts in the transformation of hydroxy group containing compounds to amides, esters, ketones, and other carbon to heteroatom or carbon to carbon transformations.

In certain embodiments, the catalytic molecules contain two bonded heteroatoms wherein one atom is nitrogen or an amide nitrogen, and the second atom is not nitrogen or carbon, such as sulfur, selenium, or tellurium.

In certain embodiments, the disclosure relates to methods of catalyzing a coupling reaction comprising mixing a) a compound comprising a hydroxy group, b) a $PR_3$, wherein $PR_3$ is a trisubsituted phosphite, trisubstituted phosphine or a phosphorus containing five member heterocycle, c) a nucleophile, and d) a catalytic molecule such as a catalytic heterocycle comprising two bonded heteroatoms wherein one heteroatom is a nitrogen and the second heteroatom is not nitrogen, under conditions such that a compound is formed comprising the nucleophile in place of the hydroxy group.

In certain embodiments, mixing includes a copper salt or other metal salts such as iron, cobalt, molybdenum.

In certain embodiments, the catalytic heterocycle is a benzo[d]isothiazol-3(2H)-one or a benzo[d][1,2]selenazol-3(2H)-one or thereof wherein a basic nitrogen atom is positioned 3 atoms from the benzo[d]isothiazol-3(2H)-one or a benzo[d][1,2]selenazol-3(2H)-one amidic nitrogen atom disulfide. In certain embodiments, the catalytic heterocycle is disulfide or deselenide wherein a basic nitrogen atom is positioned 2 or 3 atoms from the amidic nitrogen atom of the disulfide or deselenide.

In certain embodiments, mixing is done under conditions such that an amide, an amine, an ester, an ether, a ketone, or other carbon to carbon bond is formed.

In certain embodiments, the compound comprising a hydroxy group is primary or secondary alcohol or a carboxylic acid.

In certain embodiments, the nucleophile comprising a hydrogen group is a primary or secondary amine, or primary or secondary alcohol, or boronic acid.

In certain embodiments, the catalytic heterocycle is benzo[d][1,2]selenazole-3(2H)-one or derivative thereof.

In certain embodiments, the catalytic molecule is linked through a linking group to a silicate, glass, polymer, metal, particle, nanoparticle, magnetic bead, nanostructure, or other solid support.

In certain embodiments, the catalytic heterocycle has the following formula:

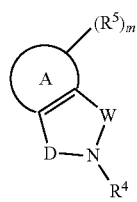

or salts thereof wherein,
A is an aryl or heteroaryl ring;
D is sulfur, selenium, or tellurium;
W is C=O, S=O, SO$_2$, P=O, PO$_2$, CH$_2$, or CR$^a$$_2$;
m is 0, 1, 2, 3, or 4;
R$^a$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl;
R$^4$ is selected from alkyl, alkenyl, alkanoyl, cyano, dialkylamino, carbocyclyl, aryl, and heterocyclyl wherein R$^4$ is optionally substituted with one or more, the same or different, R$^{40}$ or R$^{41}$;
R$^{40}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein R$^{40}$ is optionally substituted with one or more, the same or different, R$^{41}$;
R$^{41}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethyl-amino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;
R$^5$ is at each occurrence individually selected from alkyl, alkenyl, alkanoyl, halogen, nitro, suflonate, cyano, hydroxy, amino, mercapto, formyl, carboxy, sulfoxy, carbamoyl, alkoxy, alkylthio, alkylamino, dialkylamino, alkylsulfinyl, alkylsulfonyl, arylsulfonyl, carbocyclyl, aryl, and heterocyclyl wherein R$^5$ is optionally substituted with one or more, the same or different, R$^{50}$;
R$^{50}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethyl-amino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

In certain embodiments, R$^a$ is hydrogen or alkyl.
In certain embodiments, R$^4$ comprises a basic nitrogen atom positioned 2 or 3 atoms from the benzoisothiazolone amidic nitrogen atom.

In certain embodiments, the catalytic heterocycle has the following formula:

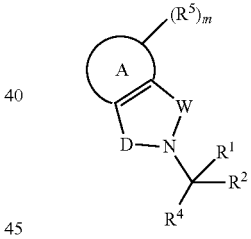

or salts thereof wherein,
A is an aryl or heteroaryl ring;
D is sulfur, selenium, or tellurium;
W is C=O, S=O, SO$_2$, P=O, PO$_2$, CH$_2$, or CR$^a$$_2$;
m is 0, 1, 2, 3, or 4;
R$^a$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl;
R$^1$ is alkyl or hydrogen;
R$^2$ is alkyl or hydrogen; or R$^1$ and R$^2$ come together to form a carbocyclyl;
R$^4$ is selected from alkyl, alkenyl, alkanoyl, cyano, dialkylamino, carbocyclyl, aryl, and heterocyclyl wherein R$^4$ is optionally substituted with one or more, the same or different, R$^{40}$ or R$^{41}$;
R$^{40}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{40}$ is optionally substituted with one or more, the same or different, $R^{41}$;

$R^{41}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

$R^5$ is at each occurrence individually selected from alkyl, alkenyl, alkanoyl, halogen, nitro, suflonate, cyano, hydroxy, amino, mercapto, formyl, carboxy, sulfoxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^5$ is optionally substituted with one or more, the same or different, $R^{50}$;

$R^{50}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

In certain embodiments, the catalytic molecule has the following formula:

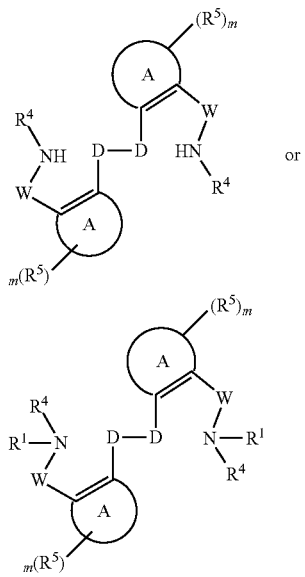

$R^a$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl;

$R^1$ is hydrogen or alkyl;

$R^4$ is selected from alkyl, alkenyl, alkanoyl, cyano, dialkylamino, carbocyclyl, aryl, and heterocyclyl wherein $R^4$ is optionally substituted with one or more, the same or different, $R^{40}$ or $R^{41}$;

$R^{40}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{40}$ is optionally substituted with one or more, the same or different, $R^{41}$;

$R^{41}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

$R^5$ is at each occurrence individually selected from alkyl, alkenyl, alkanoyl, halogen, nitro, suflonate, cyano, hydroxy, amino, mercapto, formyl, carboxy, sulfoxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^5$ is optionally substituted with one or more, the same or different, $R^{50}$;

$R^{50}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

In certain embodiments, the catalytic molecule has the following formula:

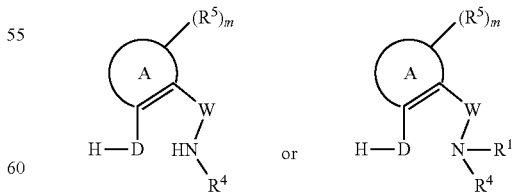

or salts thereof wherein,

A is an aryl or heteroaryl ring;

D is sulfur, selenium, or tellurium;

W is C=O, S=O, $SO_2$, P=O, $PO_2$, $CH_2$, or $CR^a_2$;

m is 0, 1, 2, 3, or 4;

or salts thereof wherein,

A is an aryl or heteroaryl ring;

D is sulfur, selenium, or tellurium;

W is C=O, S=O, $SO_2$, P=O, $PO_2$, $CH_2$, or $CR^a_2$;

m is 0, 1, 2, 3, or 4;

$R^a$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl;

$R^1$ is hydrogen or alkyl;

$R^4$ is selected from alkyl, alkenyl, alkanoyl, cyano, dialkylamino, carbocyclyl, aryl, and heterocyclyl wherein $R^4$ is optionally substituted with one or more, the same or different, $R^{40}$ or $R^{41}$;

$R^{40}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{40}$ is optionally substituted with one or more, the same or different, $R^{41}$;

$R^{41}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

$R^5$ is at each occurrence individually selected from alkyl, alkenyl, alkanoyl, halogen, nitro, suflonate, cyano, hydroxy, amino, mercapto, formyl, carboxy, sulfoxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^5$ is optionally substituted with one or more, the same or different, $R^{50}$;

$R^{50}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

In certain embodiments, the catalytic heterocycle has the following formula:

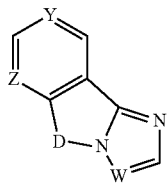

or salts thereof wherein,
Y is N, CH, or C—$R^5$;
Z is N or CH;
D is S or Se, or Te;
W is CH or N;

$R^5$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^5$ is optionally substituted with one or more, the same or different, $R^{50}$;

$R^{50}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

In certain embodiments, the catalytic heterocycle has the following formula:

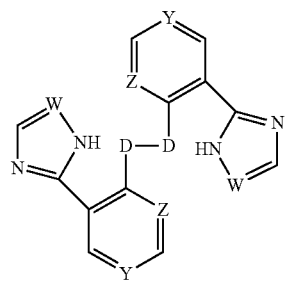

or salts thereof wherein,
Y is N, CH, or C—$R^5$;
Z is N or CH;
D is S or Se, or Te;
W is CH or N;

$R^5$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^5$ is optionally substituted with one or more, the same or different, $R^{50}$;

$R^{50}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

In certain embodiments, the catalytic heterocycle has the following formula:

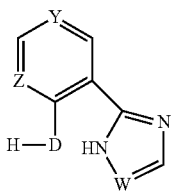

or salts thereof wherein,
Y is N, CH, or C—R⁵;
Z is N or CH;
D is S or Se, or Te;
W is CH or N;
R⁵ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein R⁵ is optionally substituted with one or more, the same or different, R⁵⁰;

R⁵⁰ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethyl-amino, acetylamino, N-methylcarbamoyl, N-ethylcarbamoyl, N,N-dimethylcarbamoyl, N,N-diethyl-carbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

In certain embodiments, the disclosure relates to methods of catalyzing a coupling reaction comprising mixing a) a compound comprising a hydroxy group, b) a PR₃, wherein PR₃ is a trisubstituted phosphite, phosphine or a phosphorus containing five member heterocycle, c) a nucleophile, d) a catalytic heterocycle comprising two bonded heteroatoms wherein one heteroatom is a nitrogen and the second heteroatom is not nitrogen, and e) a metal nanoparticle with a diameter of between 1 and 100 nm, under conditions such that a compound is formed comprising the nucleophile in place of the hydroxy group. In certain embodiments, the method further comprises adding a nickel(II) salt such as NiC₂, Ni(NO₃)₂, or Ni(OAc)₂. In certain embodiments, the reaction conditions are mixing the components in a) to e) in the presence of electromagnetic radiation of greater than 400 nm, e.g., sunlight. In certain embodiments, the nanoparticle comprises a core of Cd and a shell of S, Se, or Te.

In certain embodiments, the disclosure relates to methods of catalyzing a coupling reaction comprising mixing a) a compound comprising a hydroxy group, b) a trisubstituted phosphite, c) a nucleophile, and d) a diselenide or a catalytic heterocycle comprising two bonded heteroatoms wherein one heteroatom is a nitrogen or an amide nitrogen and the second heteroatom is sulfur, selenium, or tellurium, under conditions such that a compound is formed comprising the nucleophile in place of the hydroxy group. In certain embodiments the reaction is catalyzed in aerobic conditions.

In certain embodiments, the compound comprising a hydroxy group is the hydroxy group of a carboxylic acid. In certain embodiments, the carboxylic acid compound is an amino acid, protected amino acid, nucleotide, polynucleotide, polypeptide, or polypeptide. In certain embodiments, carboxylic acid compound is linked to a solid support.

In certain embodiments, mixing includes the addition of copper. In certain embodiments, mixing includes the addition of a nitrogen containing copper ligand selected from N-methylimidazole, N-methylmorpholine, N,N'-dimethylaminopyridine, 1,4-diazabicyclo[2.2.2]octane, and methylpyridine.

In certain embodiments, the trisubstituted phosphite is trialkylphosphite selected from trimethylphosphite, triethylphosphite, tripropylphosphite, triisopropylphosphite, tributyl phosphite, and tert-butylphoshpite.

In certain embodiments, the catalyst comprising a selenium nitrogen heterocycle is benzo[d][1,2]selenazole-3(2H)-one or derivative thereof.

In certain embodiments, the catalyst comprising a sulfur nitrogen heterocycle is benzoisothiazolone or derivative thereof.

BRIEF DESCRIPTION OF THE SEVERAL VIEWS OF THE DRAWINGS

FIG. 1D shows a table of products produced by using a catalytic redox system comprising 20 mol % organocatalyst 1g and 10 mol % CuI₂(NMI)₄ in MeCN under dry air (4 Å molecular sieves) at 50° C., a variety of amides were constructed from 1.0 equiv of a carboxylic acid, 1.2 equiv of an amine, and 1.5 equiv of triethyl phosphite. For workup and isolation, the MeCN was filtered, and the solids were washed with CH₂Cl₂. The solvents were evaporated, and the products were obtained by SiO₂ chromatography. The entries span 1 and 2° amines, aliphatic and aromatic amines, amino acids and amino alcohols/phenols. The method is compatible with oxidation-prone substrates such as alkenes, boron derivatives, and furans and indoles as well as with electron-deficient heterocycles and benzene derivatives, and it works well for amines with a significant range of $pK_a(H)$, chiral amine partners, chiral acid partners, and others. No racemization of stereocenters was observed for those substrates studied. The synthesis of peptide 3a shown in was carried out on a 5 g scale and delivered the product in 91% yield after 24 h at 50° C.

FIG. 4 illustrates the formation of ketones using a carbon nucleophile of a boronic acid intermediate. Substituted tin-based and silicon based nucleophiles are also contemplated, e.g., RSnBu3 or RSiX3, wherein X is a halogen and R is alkyl, aryl, or heterocyclic optionally substituted.

FIG. 14 illustrates benzosioseleazolones.

FIG. 15 shows catalytic data for benzosioseleazolones illustrated in FIG. 14.

DETAILED DISCUSSION

Figure 1A:
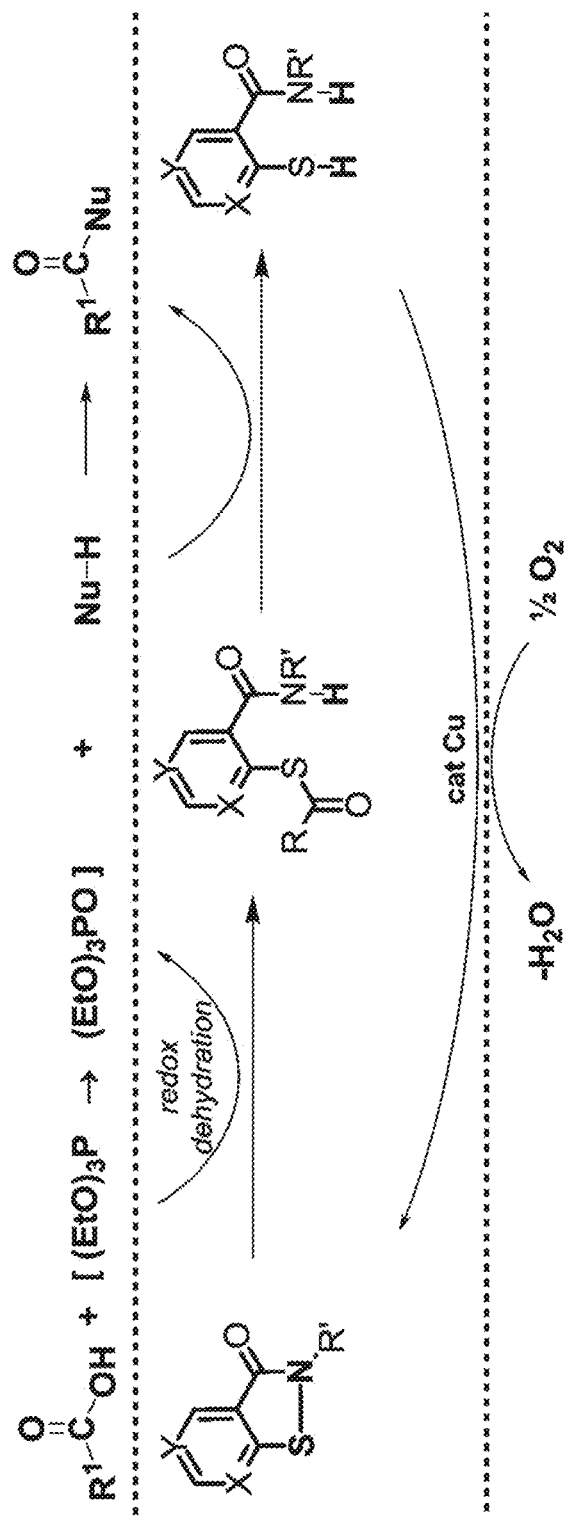
FIG. 1A illustrates certain embodiments disclosed herein for sulfur based catalysts: benzoisothiazolone (BiT)-catalyzed, redox-coupled dehydrative bond formation. Three steps include redox dehydration of R¹—OH to a thioorganic intermediate, aerobic condition desulfitative coupling to create the C—N, C—O, or C—C product, and aerobic regeneration of the BiT catalyst 1. Typical reaction conditions include mixing in solvent under N₂ or Ar, adding 4 Å mol sieves, stirring between room temp and 50° C., evaporating and triturating or partitioning between H₂O/EtOAc. Typical reaction solvents include THF, DMF, toluene, EtOAc, CH₃CN.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Terms

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise.

As used herein, the term "amino acid" refers to both naturally-occurring and synthetically modified (D-, L-, achiral or racemic) amino acids and derivatives. In some embodiments, the amino acid may be selected from the group consisting of any one or more of (D-, L-, achiral or racemic) glycine, alanine, valine, leucine, isoleucine, phenylalanine, serine, methionine, proline, tyrosine, tryptophan, lysine, arginine, histidine, aspartate, glutamate, asparagine, glutamine, cysteine, methionine, hydroxyproline, gama-carboxyglutamate, O-phosphoserine, ornithine, homoarginine and various protected derivatives thereof.

A "protecting group" refers to those moieties that are introduced into a molecule by chemical modification of a functional group in order to obtain chemoselectivity in a subsequent chemical reaction. Examples include, but are not limited to, 4-methoxy-2,3,6-trimethylphenyl)sulfonyl (Mtr), 2,2,5,7,8-pentamethyl-chroman-6-sulphonyl (Pmc), tosyl (Tos), mesitylenesulfonyl (Mts), 4,4'-dimethoxybenzhydryl (Mbh), 2,4,6-trimethoxybenzyl (Tmob), tripheylmethyl (Trt), 9-fluorenylmethyloxycarbonyl (fmoc), tert-buty (tBu), benzyl (Bzl), t-Butoxymethyl ether (Bum), (2,4-dinitrophenol) Dnp, benzyloxymethyl (Bom), benzyloxycarbonyl (Z), 2-chloro-benzyloxycarbonyl (CIZ), t-butyloxycarbonyl (Boc), formyl (CHO) or 2-bromobenzyloxycarbonyl (BrZ) and heterocycles such as succinimide, maleimide, and phathalimide.

As used herein, a "linker" refers to any molecular configuration that joins molecular moieties. It includes molecules with covalent and non-covalent interactions. A prefer linker is a polymer, i.e., molecule with repeated linking moieties. The linked moieties may be identical in structure or vary, e.g., copolymers. Linking polymers include, but are not limited to, biological polymers, polyethylene glycols, alkylacrylates, alkylacrylamides, and substituted variants.

"Saccharide" refers a sugar(s) or substituted sugar(s) exemplified by, but not limited to, ribose, riboside, glucose, glucoside, mannose, mannoside, mannoside, galactose, galactoside, talitol, taloside, rhamnitol, rhamnoside, maltose, maltoside, 2,3-dideoxyhex-2-enopyraioside, 2,3-desoxy-2,3-dehydroglucose, 2,3-desoxy-2,3-dehydroglucosediacetate, 2,3-desoxy-2,3-dehydromaltoside, 2,3-desoxy-2,3-dehydromaltoside pentaacetate, 2,3-desoxymaltoside, lactoside, lactoside tetraacetate, 2,3-desoxy-2,3-dehydrolactoside, 2,3-desoxy-2,3-dehydrolactoside pentaacetate, 2,3-desoxylactoside, glucouronate, N-acetylglucosamine, fructose, sorbose, 2-deoxygalactose, 2-deoxyglucose, maltulose, lactulose, palatinose, leucrose, turanose, lactose, mannitol, sorbitol, dulcitol, xylitol, erythritol, threitol, adonitol, arabitol, 1-aminodulcitol, 1-aminosorbitol, isomaltitol, cellobiitol, lactitol, maltitol, volemitol perseitol, glucoheptitol, alpha,alpha-glucooctitiol or combinations thereof, i.e., disaccharides, polysaccharides, and carbohydrates. Saccharides can be derivatized with molecular arrangements that facilitate synthesis (i.e., contain a protecting group, e.g., acetyl group).

The term "substrate" refers to any variety of solid surfaces. The solid surfaces may be provided in a variety of formats. For examples, the substrates may be planar or curved surfaces or be beads. In some preferred embodiments, the beads are commercially available beads such as glass beads, agarose beads, acrylic beads, plastic, or latex beads. In some embodiments, the beads are magnetic. In still other embodiments, the beads are coated with organic film(s) or metal(s) such as silver or gold. A wide variety of reaction types are available for the functionalization of solid surfaces. For example, solid surfaces constructed of a plastic such as polypropylene, can be surface derivatized by chromic acid oxidation, and subsequently converted to hydroxylated or aminomethylated surfaces. Substrates made from highly crosslinked divinylbenzene can be surface derivatized by chloromethylation and subsequent functional group manipulation. Additionally, functionalized solid surfaces can be made from etched, reduced polytetrafluoroethylene.

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, replacing an oxygen atom with a sulfur atom or replacing an amino group with a hydroxy group. Contemplated derivative include switching carbocyclic, aromatic or phenyl rings with heterocyclic rings or switching heterocyclic rings with carbocyclic, aromatic or phenyl rings, typically of the same ring size. Derivatives may be prepare by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze, all hereby incorporated by reference.

A "silylating agent" refers to an variety of silicon based reagents typically used to form a silicon bond with atoms such as oxygen, nitrogen, and sulfur, including, but not limited to, N-methyl-N-(trimethylsilyl)trifluoroacetamide, N-tert-butyldimethylsilyl-N-methyltrifluoroacetamide, 1,3-bis(chloromethyl)-1,1,3,3-tetramethyldisilazane, 1-(trimethylsilyl)imidazole, 3-trimethylsilyl-2-oxazolidinone, allyl (chloro)dimethylsilane, bromotrimethylsilane, chlorotriethylsilane, chlorotriisopropylsilane, chlorotrimethylsilane, hexaethyldisiloxane, hexamethyldisilazane, N,N'-bis(trimethylsilyl)urea, N,N-dimethyltrimethylsilylamine, N,O-bis(trimethylsilyl)acetamide, N-methyl-N-trimethylsilylacetamide, N-methyl-N-trimethylsilylheptafluorobutyramide, trimethylsilyl methanesulfonate, trimethylsilyl N,N-dimethylcarbamate, trimethylsilyl trifluoromethanesulfonate, triphenylsilane, methyl 3-trimethylsiloxy-2-butenoate, phenylchlorosilane, or triethylsilane or mixtures thereof. In certain embodiments, the silylating agent is intended to include molecules comprising of Si—S units such as silylthiols and silathianes, e.g., hexamethyldisilathiane (HMDST).

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(=O)Rb, —NRaC(=O)NRaNRb, —NRaC(=O)ORb, —NRaSO$_2$Rb, —C(=O)Ra, —C(=O)ORa, —C(=O)NRaRb, —OC(=O)NRaRb, —ORa, —SRa, —SORa, —S(=O)$_2$Ra, —OS(=O)$_2$Ra and —S(=O)$_2$ORa. Ra and Rb in this context may be the same or different and independently hydrogen, halogen hydroxy, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl. Any R group disclosed herein is contemplated to be alkyl, aryl, or heteroaryl, optionally substituted.

When used in reference to compound(s) disclosed herein, "salts" refer to derivatives of the disclosed compound(s) where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids; and the like.

As used herein, "alkyl" means a noncyclic straight chain or branched, unsaturated or saturated hydrocarbon such as those containing from 1 to 10 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Aryl" means an aromatic carbocyclic monocyclic or polycyclic ring such as phenyl or naphthyl. Polycyclic ring systems may, but are not required to, contain one or more non-aromatic rings, as long as one of the rings is aromatic.

As used herein, "heteroaryl" or "heteroaromatic" refers an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined above attached through a sulfur bridge. An example of an alkylthio is methylthio, (i.e., —S—CH$_3$).

"Alkoxy" refers to an alkyl group as defined above attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy.

"Alkylamino" refers an alkyl group as defined above attached through an amino bridge. An example of an alkylamino is methylamino, (i.e., —NH—CH$_3$).

"Alkanoyl" refers to an alkyl as defined above attached through a carbonyl bridge (i.e., —(C=O)alkyl).

"Alkylsulfonyl" refers to an alkyl as defined above attached through a sulfonyl bridge (i.e., —S(=O)$_2$alkyl) such as mesyl and the like, and "Arylsulfonyl" refers to an aryl attached through a sulfonyl bridge (i.e., —S(=O)$_2$aryl).

"Alkylsulfamoyl" refers to an alkyl as defined above attached through a sulfamoyl bridge (i.e., —S(=O)$_2$NHalkyl), and an "Arylsulfamoyl" refers to an alkyl attached through a sulfamoyl bridge (i.e., —S(=O)$_2$NHaryl).

"Alkylsulfinyl" refers to an alkyl as defined above with the indicated number of carbon atoms attached through a sulfinyl bridge (i.e. —S(=O)alkyl).

The terms "halogen" and "halo" refer to fluorine, chlorine, bromine, and iodine.

The term "aroyl" refers to an aryl group (which may be optionally substituted as described above) linked to a carbonyl group (e.g., —C(O)-aryl).

"Sulfoxy" refers to sulphonic acid attached through an oxygen bridge (i.e., —O—S(=O)$_2$O).

The term "sulfonate" refers to salt of sulfonic acid or ester thereof. (i.e., —S(=O)$_2$O$^-$ cation$^+$ —S(=O)$_2$OR).

"Ester" refers to as the oxygen bridge between two carbon atoms, wherein neither of the bridged carbon atom are a carbonyl (i.e., oxo substituted).

An unspecified "R" group is a lower alkyl, aryl, or heteroaryl, which may be optionally substituted with one or more, the same or different, substituents.

Throughout the specification, groups and substituents thereof may be chosen to provide stable moieties and compounds.

Catalytic Molecules

This disclosure relates to synthetic coupling methods using catalytic molecules containing a sulfur nitrogen bond, such as a sulfur amide nitrogen bond, typically in a heterocycle, such as substituted benzoisothiazolones and derivatives thereof, as catalysts in the transformation of hydroxy group containing compounds to amides, esters, ketones, and other carbon to heteroatom or carbon to carbon transformations. This disclosure also contemplates selenium-nitrogen and tellurium-bonded molecules, such as selenazolones and tellurazolones, as well as to deselenides and ditellurides.

In certain embodiments, the catalytic heterocycle has the following formula:

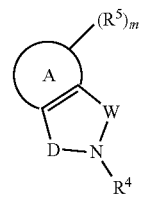

or salts thereof wherein,
A is an aryl or heteroaryl ring;
D is sulfur, selenium, or tellurium;

W is C═O, S═O, SO$_2$, P═O, PO$_2$, CH$_2$, or CR$^a$$_2$;

m is 0, 1, 2, 3, or 4;

R$^a$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl;

R$^4$ is selected from alkyl, alkenyl, alkanoyl, cyano, dialkylamino, carbocyclyl, aryl, and heterocyclyl wherein R$^4$ is optionally substituted with one or more, the same or different, R$^{40}$ or R$^{41}$;

R$^{40}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein R$^{40}$ is optionally substituted with one or more, the same or different, R$^{41}$;

R$^{41}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

R$^5$ is at each occurrence individually selected from alkyl, alkenyl, alkanoyl, halogen, nitro, suflonate, cyano, hydroxy, amino, mercapto, formyl, carboxy, sulfoxy, carbamoyl, alkoxy, alkylthio, alkylamino, dialkylamino, alkylsulfinyl, alkylsulfonyl, arylsulfonyl, carbocyclyl, aryl, and heterocyclyl wherein R$^5$ is optionally substituted with one or more, the same or different, R$^{50}$;

R$^{50}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

In certain embodiments, the catalytic molecule has the following formula:

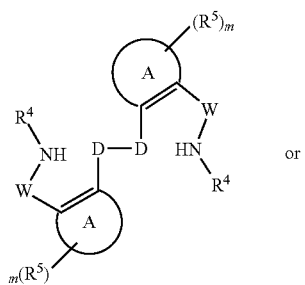

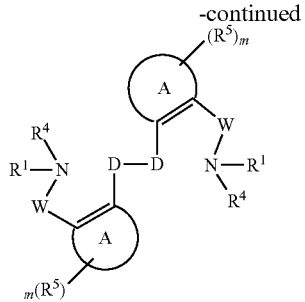

or salts thereof wherein,

A is an aryl or heteroaryl ring;

D is sulfur, selenium, or tellurium;

W is C═O, S═O, SO$_2$, P═O, PO$_2$, CH$_2$, or CR$^a$$_2$;

m is 0, 1, 2, 3, or 4;

R$^a$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl;

R$^1$ is hydrogen or alkyl;

R$^4$ is selected from alkyl, alkenyl, alkanoyl, cyano, dialkylamino, carbocyclyl, aryl, and heterocyclyl wherein R$^4$ is optionally substituted with one or more, the same or different, R$^{40}$ or R$^{41}$;

R$^{40}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein R$^{40}$ is optionally substituted with one or more, the same or different, R$^{41}$;

R$^{41}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

R$^5$ is at each occurrence individually selected from alkyl, alkenyl, alkanoyl, halogen, nitro, suflonate, cyano, hydroxy, amino, mercapto, formyl, carboxy, sulfoxy, carbamoyl, alkoxy, alkylthio, alkylamino, dialkylamino, alkylsulfinyl, alkylsulfonyl, arylsulfonyl, carbocyclyl, aryl, and heterocyclyl wherein R$^5$ is optionally substituted with one or more, the same or different, R$^{50}$;

R$^{50}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

In certain embodiments the catalytic molecule has the following formula:

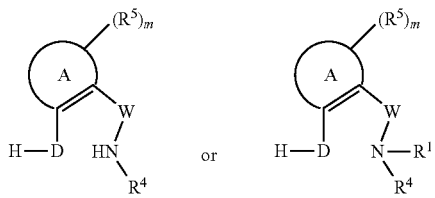 or 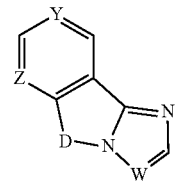

or salts thereof wherein,
A is an aryl or heteroaryl ring;
D is sulfur, selenium, or tellurium;
W is C=O, S=O, SO$_2$, P=O, PO$_2$, CH$_2$, or CR$^a$$_2$;
m is 0, 1, 2, 3, or 4;
R$^1$ is hydrogen or alkyl;
R$^a$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl;
R$^4$ is selected from alkyl, alkenyl, alkanoyl, cyano, dialkylamino, carbocyclyl, aryl, and heterocyclyl wherein R$^4$ is optionally substituted with one or more, the same or different, R$^{40}$ or R$^{41}$;
R$^{40}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein R$^{40}$ is optionally substituted with one or more, the same or different, R$^{41}$;
R$^{41}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;
R$^5$ is at each occurrence individually selected from alkyl, alkenyl, alkanoyl, halogen, nitro, suflonate, cyano, hydroxy, amino, mercapto, formyl, carboxy, sulfoxy, carbamoyl, alkoxy, alkylthio, alkylamino, dialkylamino, alkylsulfinyl, alkylsulfonyl, arylsulfonyl, carbocyclyl, aryl, and heterocyclyl wherein R$^5$ is optionally substituted with one or more, the same or different, R$^{50}$;
R$^{50}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

In certain embodiments, the catalytic heterocycle has the following formula:

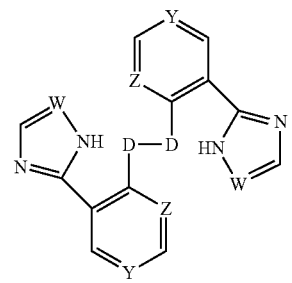

or salts thereof wherein,
Y is N, CH, or C—R$^5$;
Z is N or CH;
D is S or Se, or Te;
W is CH or N;
R$^5$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein R$^5$ is optionally substituted with one or more, the same or different, R$^{50}$;
R$^{50}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

In certain embodiments, the catalytic heterocycle has the following formula:

or salts thereof wherein,
Y is N, CH, or C—R$^5$;
Z is N or CH;
D is S or Se, or Te;
W is CH or N;
R$^5$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein R$^5$ is optionally substituted with one or more, the same or different, R$^{50}$;
R$^{50}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethyl-amino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

In certain embodiments, the catalytic heterocycle has the following formula:

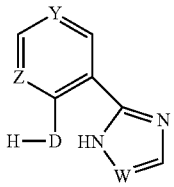

or salts thereof wherein,
Y is N, CH, or C—$R^5$;
Z is N or CH;
D is S or Se, or Te;
W is CH or N;
$R^5$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^5$ is optionally substituted with one or more, the same or different, $R^{50}$;
$R^{50}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethyl-amino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

In certain embodiments, the catalytic heterocycle has the following formula:

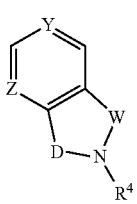

or salts thereof wherein,
Y is N, CH, or C—$R^5$;
Z is N or CH;
D is S or Se, or Te;
W is C=O, S=O, $SO_2$, P=O, $PO_2$; or W is $CH_2$ or $CR^a{}_2$;
$R^a$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl;

$R^4$ is selected from alkyl, alkenyl, alkanoyl, cyano, dialkylamino, carbocyclyl, aryl, and heterocyclyl wherein $R^4$ is optionally substituted with one or more, the same or different, $R^{40}$ or $R^{41}$;
$R^{40}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{40}$ is optionally substituted with one or more, the same or different, $R^{41}$;
$R^{41}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethyl-amino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;
$R^5$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^5$ is optionally substituted with one or more, the same or different, $R^{50}$;
$R^{50}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethyl-amino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl. In certain embodiments, W is S=O, $SO_2$, P=O, $PO_2$.

In certain embodiments, the catalytic heterocycle has the following formula:

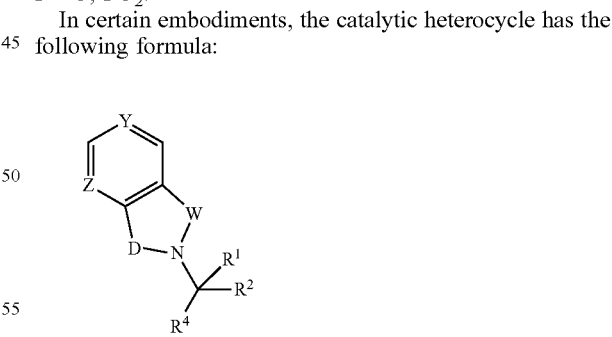

or salts thereof wherein,
Y is N, CH, or C—$R^5$;
Z is N or CH;
D is S or Se, or Te;
W is C=O, S=O, $SO_2$, P=O, $PO_2$; or W is $CH_2$ or $CR^a{}_2$;
$R^a$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl;

R¹ is alkyl or hydrogen;

R² is alkyl or hydrogen; or R¹ and R² come together to form a carbocyclyl;

R⁴ is selected from alkyl, alkenyl, alkanoyl, cyano, dialkylamino, carbocyclyl, aryl, and heterocyclyl wherein R⁴ is optionally substituted with one or more, the same or different, R⁴⁰ or R⁴¹;

R⁴⁰ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein R⁴⁰ is optionally substituted with one or more, the same or different, R⁴¹;

R⁴¹ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

R⁵ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein R⁵ is optionally substituted with one or more, the same or different, R⁵⁰;

R⁵⁰ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

In certain embodiments, the catalytic heterocycle has the following formula:

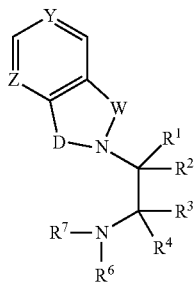

or salts wherein,

Y is N, CH, or C—R⁵;

Z is N or CH;

D is S or Se, or Te;

W is C=O, S=O, SO₂, P=O, PO₂, CH₂; or W is CH₂, or CRᵃ₂;

Rᵃ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl;

R¹, R², R³, R⁴, and R⁷ are each individually and independently hydrogen or alkyl;

R⁶ is hydrogen or alkyl; or R⁶ and R⁷ come together to form a heterocyclyl, or R⁴ and R⁶ come together to form a heterocyclyl;

R⁵ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein R⁵ is optionally substituted with one or more, the same or different, R⁵⁰;

R⁵⁰ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

In certain embodiments, the catalytic heterocycle has the following formula:

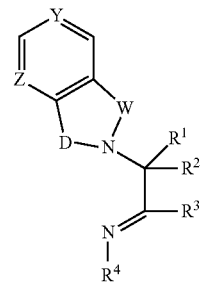

or salts wherein,

Y is N, CH, or C—R⁵;

Z is N or CH;

D is S or Se, or Te;

W is C=O, S=O, SO₂, P=O, PO₂, CH₂; or W is CH₂, or CRᵃ₂;

Rᵃ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl;

R¹ is hydrogen or alkyl;

R² is hydrogen or alkyl; or R¹ and R² come together to form a carbocyclyl;

R³ is hydrogen or alkyl;

R⁴ is hydrogen or alkyl, or R³ and R⁴ come together to form a heterocyclyl;

R⁵ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^5$ is optionally substituted with one or more, the same or different, $R^{50}$;

$R^{50}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

In certain embodiments, the catalytic heterocycle has the following formula:

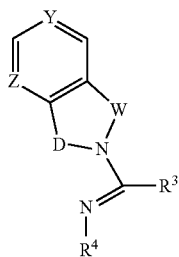

or salts wherein,
Y is N, CH, or C—$R^5$;
Z is N or CH;
D is S or Se, or Te;
W is C=O, S=O, SO$_2$, P=O, PO$_2$, CH$_2$; or W is CH$_2$, or CR$^a{}_2$;
$R^a$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl;
$R^3$ is hydrogen or alkyl;
$R^4$ is hydrogen or alkyl, or $R^3$ and $R^4$ come together to form a heterocyclyl;
$R^5$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^5$ is optionally substituted with one or more, the same or different, $R^{50}$;
$R^{50}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

In certain embodiments, the catalytic heterocycle has the following formula:

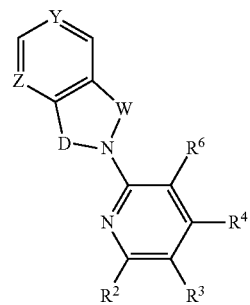

or salts wherein,
Y is N, CH, or C—$R^5$;
Z is N or CH;
D is S or Se, or Te;
W is C=O, S=O, SO$_2$, P=O, PO$_2$, CH$_2$; or W is CH$_2$, or CR$^a{}_2$;
$R^a$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl;
$R^2$, $R^3$, $R^4$, $R^5$, and $R^6$ are each individually and independently selected from hydrogen, alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^5$ is optionally substituted with one or more, the same or different, $R^{50}$;
$R^{50}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

In certain embodiments, the catalytic molecule has the following formula:

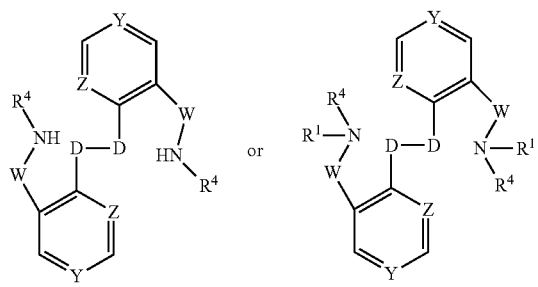

or salts thereof wherein,
Y is N, CH, or C—$R^5$;
Z is N or CH;
D is S or Se, or Te;
W is C=O, S=O, SO$_2$, P=O, PO$_2$; or W is CH$_2$, or CR$^a{}_2$;

$R^a$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl;

$R^1$ is hydrogen or alkyl;

$R^4$ is selected from alkyl, alkenyl, alkanoyl, cyano, dialkylamino, carbocyclyl, aryl, and heterocyclyl wherein $R^4$ is optionally substituted with one or more, the same or different, $R^{40}$ or $R^{41}$;

$R^{40}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{40}$ is optionally substituted with one or more, the same or different, $R^{41}$;

$R^{41}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

$R^5$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^5$ is optionally substituted with one or more, the same or different, $R^{50}$;

$R^{50}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl. In certain embodiments, W is S=O, SO$_2$, P=O, PO$_2$.

In certain embodiments, the catalytic molecule has the following formula:

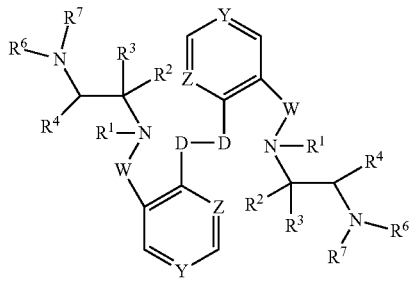

or salts thereof wherein,
Y is N, CH, or C—$R^5$;
Z is N or CH;
D is S or Se, or Te;
W is C=O, S=O, SO$_2$, P=O, PO$_2$; or W is CH$_2$, or CR$^a_2$;

$R^a$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl;

$R^1$, $R^2$, $R^3$, $R^4$, and Reach individually and independently alkyl or hydrogen;

$R^6$ is alkyl or hydrogen; or $R^6$ and $R^7$ come together to form a heterocyclyl; or $R^6$ and $R^4$ come together to form a heterocyclyl;

$R^5$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^5$ is optionally substituted with one or more, the same or different, $R^{50}$;

$R^{50}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

In certain embodiments, the catalytic molecule has the following formula:

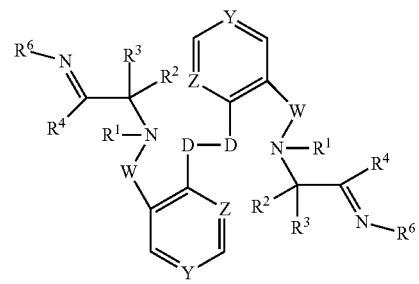

or salts thereof wherein,
Y is N, CH, or C—$R^5$;
Z is N or CH;
D is S or Se, or Te;
W is C=O, S=O, SO$_2$, P=O, PO$_2$; or W is CH$_2$, or CR$^a_2$;

$R^a$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl;

$R^1$, $R^2$, $R^3$, and $R^4$, each individually and independently, are alkyl or hydrogen;

$R^6$ is alkyl or hydrogen; or $R^6$ and $R^4$ come together to form a heterocyclyl;

$R^5$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^5$ is optionally substituted with one or more, the same or different, $R^{50}$;

$R^{50}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethyl-amino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

In certain embodiments, the catalytic molecule has the following formula:

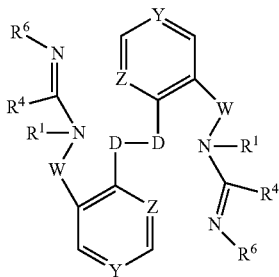

or salts thereof wherein,
Y is N, CH, or C—$R^5$;
Z is N or CH;
D is S or Se, or Te;
W is C=O, S=O, SO$_2$, P=O, PO$_2$; or W is CH$_2$, or CR$^a{}_2$;
$R^a$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl;
$R^1$ and $R^4$, each individually and independently, are alkyl or hydrogen;
$R^6$ is alkyl or hydrogen; or $R^6$ and $R^4$ come together to form a heterocyclyl;
$R^5$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^5$ is optionally substituted with one or more, the same or different, $R^{50}$;
$R^{50}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethyl-amino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

In certain embodiments, the catalytic molecule has the following formula:

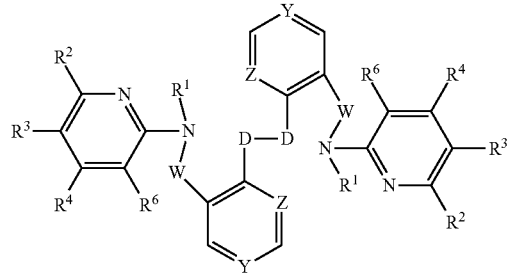

or salts thereof wherein,
Y is N, CH, or C—$R^5$;
Z is N or CH;
D is S or Se, or Te;
W is C=O, S=O, SO$_2$, P=O, PO$_2$; or W is CH$_2$, or CR$^a{}_2$;
$R^a$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl;
$R^1$ is hydrogen or alkyl;
$R^2$, $R^3$, $R^4$, $R^5$, and $R^6$ are each individually and independently selected from hydrogen, alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^5$ is optionally substituted with one or more, the same or different, $R^{50}$;
$R^{50}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethyl-amino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

In certain embodiments, the catalytic molecule has the following formula:

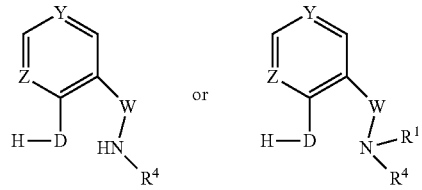

wherein,
Y is N, CH, or C—$R^5$;
Z is N or CH;
D is S or Se, or Te;
W is C=O, S=O, SO$_2$, P=O, PO$_2$; or W is CH$_2$, or CR$^a{}_2$;

$R^a$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl;

$R^1$ is hydrogen or alkyl;

$R^4$ is selected from alkyl, alkenyl, alkanoyl, cyano, dialkylamino, carbocyclyl, aryl, and heterocyclyl wherein $R^4$ is optionally substituted with one or more, the same or different, $R^{40}$ or $R^{41}$;

$R^{40}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{40}$ is optionally substituted with one or more, the same or different, $R^{41}$;

$R^{41}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethyl-amino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

$R^5$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^5$ is optionally substituted with one or more, the same or different, $R^{50}$;

$R^{50}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethyl-amino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl. In certain embodiments, W is S=O, $SO_2$, P=O, $PO_2$.

In certain embodiments, $R^5$ is an electron with drawing group selected from nitro, sulfonate, quaternary amine, trihalo alkyl, trifluoromethyl, cyano, alkanoyl, formyl, carboxy, carbamoyl, alkylsulfinyl, alkylsulfonyl, and arylsulfonyl wherein $R^5$ is optionally substituted with one or more, the same or different, $R^{50}$.

In certain embodiments, the catalytic heterocycle has the following formula:

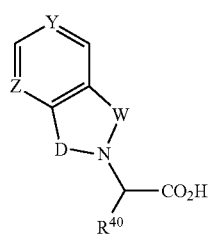

or salts thereof wherein,

D is sulfur, selenium, or tellurium;

Y is N, CH, or C—$R^5$;

Z is N or CH;

W is C=O, S=O, $SO_2$, P=O, $PO_2$; or W is $CH_2$, or $CR^a_2$;

$R^a$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl;

$R^{40}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{40}$ is optionally substituted with one or more, the same or different, $R^{41}$;

$R^{41}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethyl-amino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

$R^5$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^5$ is optionally substituted with one or more, the same or different, $R^{50}$;

$R^{50}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethyl-amino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

In certain embodiments, $R^5$ is an electron with drawing group selected from nitro, sulfonate, quaternary amine, trihalo alkyl, trifluoromethyl, cyano, alkanoyl, formyl, carboxy, carbamoyl, alkylsulfinyl, alkylsulfonyl, and arylsulfonyl wherein $R^5$ is optionally substituted with one or more, the same or different, $R^{50}$.

In certain embodiments, the catalytic molecule has the following formula:

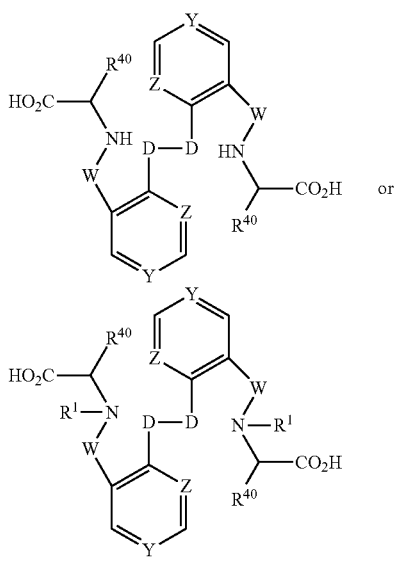

or salts thereof wherein,

D is sulfur, selenium, or tellurium;

Y is N, CH, or C—$R^5$;

Z is N or CH;

W is C=O, S=O, $SO_2$, P=O, $PO_2$; or W is $CH_2$, or $CR^a_2$;

$R^a$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl;

$R^1$ is hydrogen or alkyl;

$R^{40}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{40}$ is optionally substituted with one or more, the same or different, $R^{41}$;

$R^{41}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

$R^5$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^5$ is optionally substituted with one or more, the same or different, $R^{50}$;

$R^{50}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

In certain embodiments, $R^5$ is an electron with drawing group selected from nitro, sulfonate, quaternary amine, trihalo alkyl, trifluoromethyl, cyano, alkanoyl, formyl, carboxy, carbamoyl, alkylsulfinyl, alkylsulfonyl, and arylsulfonyl wherein $R^5$ is optionally substituted with one or more, the same or different, $R^{50}$.

In certain embodiments, the catalytic heterocycle has the following formula:

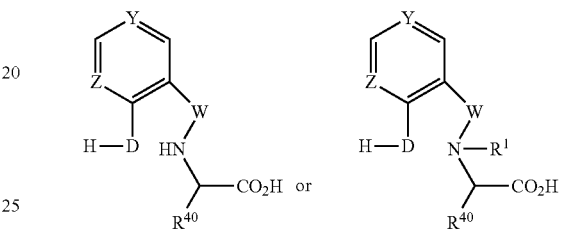

or salts thereof wherein,

D is sulfur, selenium, or tellurium;

Y is N, CH, or C—$R^5$;

Z is N or CH;

W is C=O, S=O, $SO_2$, P=O, $PO_2$; or W is $CH_2$, or $CR^a_2$;

$R^a$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl;

$R^1$ is hydrogen or alkyl;

$R^{40}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{40}$ is optionally substituted with one or more, the same or different, $R^{41}$;

$R^{41}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

$R^5$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^5$ is optionally substituted with one or more, the same or different, $R^{50}$;

$R^{50}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

In certain embodiments, $R^5$ is an electron with drawing group selected from nitro, sulfonate, quaternary amine, trihalo alkyl, trifluoromethyl, cyano, alkanoyl, formyl, carboxy, carbamoyl, alkylsulfinyl, alkylsulfonyl, and arylsulfonyl wherein $R^5$ is optionally substituted with one or more, the same or different, $R^{50}$.

In any of the embodiments disclosed herein the catalysts may be in salt forms.

Methods of Use

In certain embodiments, the disclosure relates to methods of catalyzing a coupling reaction comprising mixing a) a compound comprising a hydroxy group, b) a trisubstituted phosphite, c) a nucleophile, and d) a catalytic molecule comprising two bonded atoms wherein one atom is an amide nitrogen and the second atom is not nitrogen, such as a sulfur, under conditions such that a compound is formed comprising the nucleophile in place of the hydroxy group.

In certain embodiments, the catalytic molecule comprising two bonded atoms wherein one atom is an amide nitrogen and the second atom is not nitrogen is a catalytic heterocycle comprising two bonded heteroatoms wherein one heteroatom is an amide nitrogen and the second heteroatom is not nitrogen, such as a sulfur, amide heterocycle, In certain embodiments, the disclosure relates to methods of forming an amide or ester comprising mixing a) a compound comprising a carboxylic acid, b) a trialkylphosphite or other phosphorus containing reagent, c) an amine or an alcohol, d) a catalytic heterocycle or molecule disclosed herein, and e) copper or salt thereof, under conditions such that an amide or an ester is formed.

Further embodiments include the synthesis of simple as well as complex cyclic and acyclic peptides, the construction of glycopeptides, for peptide ligation.

The reagents disclosed herein may also be employed to ligate an amino acid, peptide or protein group to a carbohydrate group, which may be a mono-, di-, tri- or polysaccharide, or to a nucleoside. The reagents of this disclosure may also be employed to ligate an amino acid, a peptide or protein group to a reporter group, tag or label (e.g., a group whose presence can be detected by optical or mass spectrometry or other instrumental method), including a fluorescent or phosphorescent group, an isotopic label or a radiolabel.

The chemistry of the present disclosure may be suitably employed for the formation of cyclic peptides as well for macrolactamization reactions.

In certain embodiments, the phosphorus containing five, four, or three member heterocycle has the following formula:

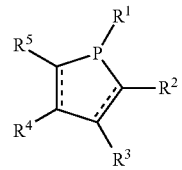

wherein, the dotted lines within the ring represent a single or double bond, $R^1$ is alkyl, aryl, or heterocyclyl, wherein $R^1$ is optionally substituted with one or more, the same or different $R^{70}$;

$R^2$, $R^3$, $R^4$, and $R^5$ are each individually and independently hydrogen, alkyl, aryl, or heterocyclyl optionally substituted with one or more substituents, or $R^2$ and $R^3$ come together to form an aryl, carbocyclyl, or heterocyclyl, or $R^3$ and $R^4$ come together to form an aryl, carbocyclyl, or heterocyclyl, or $R^4$ and $R^5$ come together to form an aryl, carbocyclyl, or heterocyclyl, wherein $R^2$, $R^3$, $R^4$, and $R^5$ are optionally substituted with one or more, the same or different $R^{70}$;

$R^{70}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{70}$ is optionally substituted with one or more, the same or different, $R^{71}$;

$R^{71}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl In certain embodiments, the compound comprising a carboxylic acid, has the following formula:

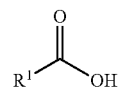

wherein, $R^1$ is selected from alkyl, alkenyl, alkanoyl, cyano, carboxy, alkylamino, dialkylamino, carbocyclyl, aryl, heterocyclyl, amino acid, polypeptide and wherein $R^1$ is optionally substituted with one or more, the same or different, $R^{10}$ or $R^{15}$;

$R^{10}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{10}$ is optionally substituted with one or more, the same or different, $R^{11}$ or $R^{15}$;

$R^{11}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{11}$ is optionally substituted with one or more, the same or different, $R^{12}$ or $R^{15}$;

$R^{12}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{12}$ is optionally substituted with one or more, the same or different, $R^{13}$ or $R^{15}$;

$R^{13}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{13}$ is optionally substituted with one or more, the same or different, $R^{14}$ or $R^{15}$;

$R^{14}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{14}$ is optionally substituted with one or more, the same or different, $R^{15}$; and $R^{15}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

In some embodiments, a compound comprising a hydroxy group is a compound comprising the following formula:

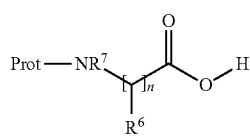

or salts thereof wherein,

Prot is a protecting group, peptide, or linker to a substrate or biological material, or $R^8$;

n is 1, 2, 3, 4, 5, or 6;

each $R^6$ is independently selected from hydrogen, alkyl, hydroxyalkyl, thiolalkyl, aminoalkyl, selenoalkyl, carboxylalkyl, aryl, or heterocyclyl, and wherein $R^6$ is optionally substituted by one or more, the same or different, $R^{60}$;

$R^7$ is hydrogen, alkyl, acyl, or $R^7$ and Prot and the attached atoms form a protecting group comprising a 4 to 7 member heterocyclic ring such as a succinimide, maleimide, or phthalimide which may be substituted with one or more, the same or different, substituents, such as one or more, the same or different, $R^{60}$ or or $R^6$ and $R^7$ and the atoms to which they are attached to form a 4-7 membered heterocyclic ring optionally substituted with one or more, the same or different, $R^{60}$;

$R^{60}$ is independently selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{60}$ is optionally substituted with $R^{61}$;

$R^{61}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl; and $R^8$ is alkyl, alkanoyl, formyl, alkylcarboxy, alkylcarbamoyl wherein $R^8$ is optionally substituted with one or more, the same or different, $R^{80}$;

$R^{80}$ is independently selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{80}$ is optionally substituted with one or more, the same or different, $R^{81}$; and $R^{81}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

In certain embodiments, $R^6$ and $R^7$ or $R^7$ and Prot form a 5 or 6 membered ring.

In certain embodiments, Prot is tert-butoxycarbonyl (Boc) or fluorenylmethyloxycarbonyl (Fmoc).

In certain embodiments, n is 1 or 2.

In certain embodiments, the biological material is a peptide, enzyme, receptor, nucleic acid, cell, antibody, saccharide, polysaccharide, or glycopeptide.

In certain embodiments, the linker is a peptide, a nucleic acid, hydrocarbon, polyethylene glycol, polysaccharide, acrylate polymer, or other polymer.

In some embodiments, a compound comprising a hydroxy group selected from N-alpha-Boc-alanine, N-beta-Boc-beta-alanine, N-alpha-Boc-N-alpha-methyl-alanine, N-alpha-Boc-alpha-aminobutyric acid, N-Boc-4-aminobutanoic acid, N-alpha-Boc-alpha-aminoisobutyric acid, N-alpha-Boc-$N^G$-(4-Methoxy-2,3,6 trimethylbenzenesulfonyl)-arginine, N-alpha-Boc-$N^G$-nitro-arginine, N-alpha-Boc-$N^G$-tosyl-arginine, N-alpha-Boc-$N^G,N^G$-bis-CBZ-arginine, N-alpha-Boc-asparagine, N-alpha-Boc-asparagine, N-alpha-Boc-beta-trityl-asparagine, N-alpha-Boc-N-beta-xanthyl-asparagine, N-alpha-Boc-isoasparagine-, N-alpha-Boc-aspartic acid beta-I-adamantyl ester, N-alpha-Boc-aspartic acid beta-2-adamantyl ester, N-alpha-Boc-aspartic acid alpha-benzyl ester, N-alpha-Boc-N-alpha-methyl-valine, N-alpha-Boc-valine, N-Boc-6-aminohexanoic acid, N-alpha-Boc-tert-leucine, N-alpha-Boc-S-acetamidomethyl-cysteine, N-alpha-Boc-S-benzyl-cysteine, N-alpha-Boc-S-p-methylbenzyl-cysteine, N-alpha-Boc-S-p-methoxybenzyl-cysteine, N-alpha-Boc-S-trityl-cysteine, N-alpha-Boc-beta-cyclohexyl-alanine, N-alpha-Boc-glutamic acid alpha-benzyl ester, N-alpha-Bocglutamic acid gama-benzyl ester, N-alpha-Boc-glutamic acid gama-cyclohexyl ester, N-alpha-Boc-glutamic acid gama-tert-butyl ester, N-alpha-Boc-gama-trityl-glutamine, N-alpha-Boc-gama-xanthyl-glutamine, N-alpha-N-im-di-Boc-histidine, N-alpha-Boc-N-im-tosyl-histidine, N-alpha-Boc-N-im-dinitrophenyl-histidine, N-alpha-Boc-N-im-trityl-histidine, N-alpha-Boc-trans-4-hydroxyproline, N-alpha-Boc-glycine, N-alpha-Boc-isoleucine, N-alpha-Boc-N-epsilon-acetyl-lysine, N-alpha,epsilon-di-Boc-lysine, N-alpha-Boc-N-epsilon-2-chloro-CBZ-lysine, N-alpha-Boc-N-epsilon-trifluoroacetyl-lysine, N-alpha-Boc-leucine, N-alpha-Boc-methionine-sulfone, N-alpha-Boc-methionine, N-alpha-Boc-methionine-sulfoxide, N-alpha-Boc-N-alpha-methyl-norleucine, N-alpha-Boc-norleucine, N-alpha-Boc-norvaline, N-alpha-Boc-3,4-dehydro-proline, N-alpha-Boc-proline, N-alpha-Boc-N-alpha-methyl-phenylalanine, N-alpha-Boc-4-chloro-phenylalanine, N-alpha-Boc-phenylalanine, N-alpha-Boc-phenylglycine, N-alpha-Boc-N-δ-benzyloxycarbonyl-ornithine, N-alpha-Boc-sarcosine, N-alpha-Boc-O-benzyl-serine, N-alpha-Boc-O-methyl-serine, N-alpha-Boc-O-tert-butyl-serine, N-1-Boc-1,2,3,4,-tetrahydro-isoquinoline-3-carboxylic acid alpha, N-alpha-Boc-N-in-Boc-trypophan, N-alpha-Boc-N-in-formyl-tryptophan, N-alpha-Boc-N-in-mesitylene-2-sulfonyl-tryptophan, N-alpha-Boc-tyrosine, N-alpha-Boc-N-alpha-methyl-O-benzyl-tyrosine, N-alpha-Boc-O-2-bromobenzyloxycarbonyl-tyrosine, N-alpha-Boc-O-benzyl-tyrosine, N-alpha-Boc-O-2,6-dichlorobenzyl-tyrosine, N-alpha-Boc-O-ethyl-tyrosine, N-alpha-Boc-O-methyl-tyrosine, N-alpha-Boc-O-tert-butyl-tyrosine, N-alpha-Boc-O-benzyl-threonine, and N-alpha-Boc-threonine, N-alpha-Fmoc-alanine, N-beta-Fmoc-beta-alanine, N-alpha-Fmoc-N-alpha-methyl-alanine, N-alpha-Fmoc-alpha-aminobutyric acid, N-Fmoc-4-aminobutanoic acid, N-alpha-Fmoc-alpha-aminoisobutyric acid, N-alpha-Fmoc-N$^G$-(4-Methoxy-2,3,6 trimethylbenzenesulfonyl)-arginine, N-alpha-Fmoc-N$^G$-nitro-arginine, N-alpha-Fmoc-N$^G$-tosyl-arginine, N-alpha-Fmoc-N$^G$,N$^G$-bis-CBZ-arginine, N-alpha-Fmoc-asparagine, N-alpha-Fmoc-asparagine, N-alpha-Fmoc-beta-trityl-asparagine, N-alpha-Fmoc-N-beta-xanthyl-asparagine, N-alpha-Fmoc-isoasparagine, N-alpha-Fmoc-aspartic acid beta-1-adamantyl ester, N-alpha-Fmoc-aspartic acid beta-2-adamantyl ester, N-alpha-Fmoc-aspartic acid alpha-benzyl ester, N-alpha-Fmoc-N-alpha-methyl-valine, N-alpha-Fmoc-valine, Fmoc-6-aminohexanoic acid, N-alpha-Fmoc-tert-leucine, N-alpha-Fmoc-S-acetamidomethyl-cysteine, N-alpha-Fmoc-S-benzyl-cysteine, N-alpha-Fmoc-S-p-methylbenzyl-cysteine, N-alpha-Fmoc-S-p-methoxybenzyl-cysteine, N-alpha-Fmoc-S-trityl-cysteine, N-alpha-Fmoc-beta-cyclohexyl-alanine, N-alpha-Fmoc-glutamic acid alpha-benzyl ester, N-alpha-Fmoc-glutamic acid gama-benzyl ester, N-alpha-Fmoc-glutamic acid gama-cyclohexyl ester, N-alpha-Fmoc-glutamic acid gama-tert-butyl ester, N-alpha-Fmoc-gama-trityl-glutamine, N-alpha-Fmoc-gama-xanthyl-glutamine, N-alpha-N-im-di-Fmoc-histidine, N-alpha-Fmoc-N-im-tosyl-histidine, N-alpha-Fmoc-N-im-dinitrophenyl-histidine, N-alpha-Fmoc-N-im-trityl-histidine, N-alpha-Fmoc-trans-4-hydroxyproline, N-alpha-Fmoc-glycine, N-alpha-Fmoc-isoleucine, N-alpha-Fmoc-N-epsilon-acetyl-lysine, N-alpha,epsilon-di-Fmoc-lysine, N-alpha-Fmoc-N-epsilon-2-chloro-CBZ-lysine, N-alpha-Fmoc-N-epsilon-trifluoroacetyl-lysine, N-alpha-Fmoc-leucine, N-alpha-Fmoc-methionine-sulfone, N-alpha-Fmoc-methionine, N-alpha-Fmoc-methionine-sulfoxide, N-alpha-Fmoc-N-alpha-methyl-norleucine, N-alpha-Fmoc-norleucine, N-alpha-Fmoc-norvaline, N-alpha-Fmoc-3,4-dehydro-proline, N-alpha-Fmoc-proline, N-alpha-Fmoc-N-alpha-methyl-phenylalanine, N-alpha-Fmoc-4-chloro-phenylalanine, N-alpha-Fmoc-phenylalanine, N-alpha-Fmoc-phenylglycine, N-alpha-Fmoc-N-6-benzyloxycarbonyl-ornithine, N-alpha-Fmoc-sarcosine, N-alpha-Fmoc-O-benzyl-serine, N-alpha-Fmoc-O-methyl-serine, N-alpha-Fmoc-O-tert-butyl-serine, N-1-Fmoc-1,2,3,4,-tetrahydro-isoquinoline-3-carboxylic acid, N-alpha-Fmoc-N-in-Fmoc-trypophan, N-alpha-Fmoc-N-in-formyl-tryptophan, N-alpha-Fmoc-N-in-mesitylene-2-sulfonyl-tryptophan, N-alpha-Fmoc-tyrosine, N-alpha-Fmoc-N-alpha-methyl-O-benzyl-tyrosine, N-alpha-Fmoc-O-2-bromobenzyloxycarbonyl-tyrosine, N-alpha-Fmoc-O-benzyl-tyrosine, N-alpha-Fmoc-O-2,6-dichlorobenzyl-tyrosine, N-alpha-Fmoc-O-ethyl-tyrosine, N-alpha-Fmoc-O-methyl-tyrosine, N-alpha-Fmoc-O-tert-butyl-tyrosine, N-alpha-Fmoc-O-benzyl-threonine, and N-alpha-Fmoc-threonine or derivatives thereof.

In certain embodiments, the disclosure relates to any of the above carboxylic acids that are a S-(2-(isopropylcarbamoyl)-4-nitrophenyl)thioate, S-(2-(isopropylcarbamoyl)-4-sulfonic acid)thioate, S-(2-(alkylcarbamoyl) phenyl)thioate, S-(2-(phenylcarbamoyl)phenyl)thioate, S-(2-((2,6-dimethylphenyl) carbamoyl)phenyl)thioate, S-(2-((2,6-dimethylphenyl)carbamoyl)-4-nitrophenyl)thioate or derivative thereof.

In some embodiments the disclosure relates to a compound comprising the following formula:

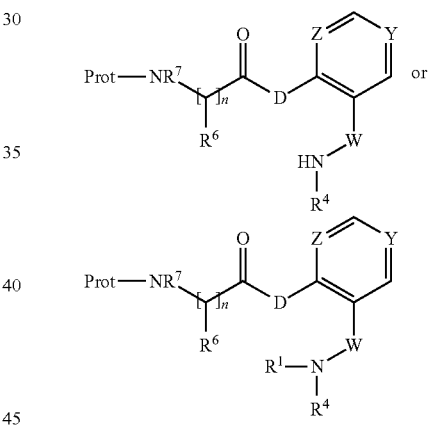

or salts thereof wherein,

Prot is a protecting group, peptide, or linker to a substrate or biological material, or $R^g$;

n is 1, 2, 3, 4, 5, or 6;

D is sulfur, selenium, or tellurium;

Y is N, CH, or C—$R^5$;

Z is N or CH;

W is C=O, S=O, SO2, P=O, PO$_2$, CH$_2$, or CR$^a_2$;

$R^a$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl;

$R^1$ is hydrogen or alkyl;

$R^4$ is selected from alkyl, alkenyl, alkanoyl, cyano, dialkylamino, carbocyclyl, aryl, and heterocyclyl wherein $R^4$ is optionally substituted with one or more, the same or different, $R^{40}$ or $R^{41}$;

$R^{40}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{40}$ is optionally substituted with one or more, the same or different, $R^{41}$;

$R^{41}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

$R^5$ is selected from alkyl, alkenyl, alkanoyl, halogen, nitro, sulfonate, cyano, hydroxy, amino, mercapto, formyl, carboxy, sulfoxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^5$ is optionally substituted with one or more, the same or different, $R^{50}$;

$R^{50}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

each $R^6$ is independently selected from hydrogen, alkyl, hydroxyalkyl, thiolalkyl, aminoalkyl, selenoalkyl, carboxylalkyl, aryl, or heterocyclyl, and wherein $R^6$ is optionally substituted by one or more, the same or different, $R^{60}$;

$R^7$ is selected from hydrogen, alkyl, acyl, or $R^7$ and Prot and the attached atoms form a protecting group comprising a 4 to 7 member heterocyclic ring such as a succinimide, maleimide, or phthalimide which may be substituted with one or more, the same or different, substituents, such as one or more, the same or different, $R^{60}$ or or $R^6$ and $R^7$ and the atoms to which they are attached to form a 4-7 membered heterocyclic ring optionally substituted with one or more, the same or different, $R^{60}$;

$R^{60}$ is independently selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{60}$ is optionally substituted with $R^{61}$;

$R^{61}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl; and $R^8$ is alkyl, alkanoyl, formyl, alkylcarboxy, alkylcarbamoyl wherein $R^8$ is optionally substituted with one or more, the same or different, $R^{80}$;

$R^{80}$ is independently selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{80}$ is optionally substituted with one or more, the same or different, $R^{81}$; and $R^{81}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

In certain embodiments, $R^5$ is an electron with drawing group selected from nitro, sulfonate, quaternary amine, trihalo alkyl, trifluoromethyl, cyano, alkanoyl, formyl, carboxy, carbamoyl, alkylsulfinyl, alkylsulfonyl, and arylsulfonyl wherein $R^5$ is optionally substituted with one or more, the same or different, $R^{50}$.

In certain embodiments, $R^5$ is $NO_2$ or other electron withdrawing group such as a carbon oxide, sulfur oxide, phosphorus oxide, or nitrogen oxide, $NO_2$, $(C=O)R^{50}$, $(C=O)NHR^{50}$, $(C=O)OR^{50}$, $(C=O)SR^{50}$, $SO_2R^{50}$, $(S=O)R^{50}$, $PO_2R^{50}$, $(P=O)R^{50}_2$, $(P=O)(OR^{50})_2$.

In some embodiments, $R^4$ is aryl or heteroaryl wherein $R^4$ is optionally substituted with one or more, the same or different, $R^4$ or $R^{41}$.

In some embodiments, the disclosure relates to a compound comprising the following formula:

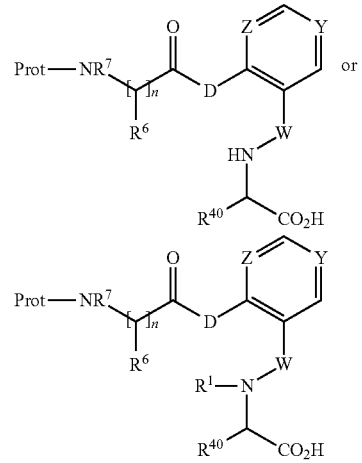

or salts thereof wherein,

Prot is a protecting group, peptide, or linker to a substrate or biological material, or $R^8$;

n is 1, 2, 3, 4, 5, or 6;

D is sulfur, selenium, or tellurium;

Y is N, CH, or C—$R^5$;

Z is N or CH;

W is C=O, S=O, SO2, P=O, PO_2, CH_2, or $CR^a_2$;

$R^a$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl;

$R^1$ is hydrogen or alkyl;

$R^{40}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{40}$ is optionally substituted with one or more, the same or different, $R^{41}$;

$R^{41}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

$R^5$ is selected from alkyl, alkenyl, alkanoyl, halogen, nitro, cyano, hydroxy, amino, mercapto, sulfonate, formyl, carboxy, carbamoyl, alkoxy, alkylthio, alkylamino, dialkylamino, sulfoxy, alkylsulfinyl, alkylsulfonyl, arylsulfonyl, carbocyclyl, aryl, and heterocyclyl wherein $R^5$ is optionally substituted with one or more, the same or different, $R^{50}$;

$R^{50}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

each $R^6$ is independently selected from hydrogen, alkyl, hydroxyalkyl, thiolalkyl, aminoalkyl, selenoalkyl, carboxylalkyl, aryl, or heterocyclyl, and wherein $R^6$ is optionally substituted by one or more, the same or different, $R^{60}$;

$R^7$ is selected from hydrogen, alkyl, acyl, or $R^7$ and Prot and the attached atoms form a protecting group comprising a 4 to 7 member heterocyclic ring such as a succinimide, maleimide, or phthalimide which may be substituted with one or more, the same or different, substituents, such as one or more, the same or different, $R^{60}$ or or $R^6$ and $R^7$ and the atoms to which they are attached to form a 4-7 membered heterocyclic ring optionally substituted with one or more, the same or different, $R^{60}$;

$R^{60}$ is independently selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{60}$ is optionally substituted with $R^{61}$;

$R^{61}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl; and $R^8$ is alkyl, alkanoyl, formyl, alkylcarboxy, alkylcarbamoyl wherein $R^8$ is optionally substituted with one or more, the same or different, $R^{80}$;

$R^{80}$ is independently selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{80}$ is optionally substituted with one or more, the same or different, $R^{81}$; and $R^{81}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

In certain embodiments, $R^5$ is an electron with drawing group selected from nitro, sulfonate, quaternary amine, trihalo alkyl, trifluoromethyl, cyano, alkanoyl, formyl, carboxy, carbamoyl, alkylsulfinyl, alkylsulfonyl, and arylsulfonyl wherein $R^5$ is optionally substituted with one or more, the same or different, $R^{50}$.

In certain embodiment, the amine or the alcohol has the following formula:

wherein,

X is O, NH, or $NR^3$;

$R^2$ is selected from alkyl, alkenyl, alkanoyl, cyano, carboxy, alkylamino, dialkylamino, carbocyclyl, aryl, and heterocyclyl wherein $R^2$ is optionally substituted with one or more, the same or different, $R^{20}$ or $R^{25}$;

$R^{20}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{20}$ is optionally substituted with one or more, the same or different, $R^{21}$ or $R^{25}$;

$R^{21}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{21}$ is optionally substituted with one or more, the same or different, $R^{22}$ or $R^{25}$;

$R^{22}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{22}$ is optionally substituted with one or more, the same or different, $R^{23}$ or $R^{25}$;

$R^{23}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{23}$ is optionally substituted with one or more, the same or different, $R^{24}$ or $R^{25}$;

$R^{24}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{24}$ is optionally substituted with one or more, the same or different, $R^{25}$;

$R^{25}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

$R^3$ is selected from alkyl, alkenyl, alkanoyl, cyano, carbocyclyl, aryl, and heterocyclyl wherein $R^3$ is optionally substituted with one or more, the same or different, $R^{30}$ or $R^{31}$;

$R^{30}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{30}$ is optionally substituted with one or more, the same or different, $R^{31}$; and $R^{31}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

In certain embodiments, the amide or ester has the formula

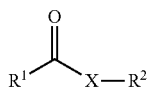

wherein,

X is O, NH, or $NR^3$;

$R^1$ is selected from alkyl, alkenyl, alkanoyl, cyano, carboxy, alkylamino, dialkylamino, carbocyclyl, aryl, and heterocyclyl wherein $R^1$ is optionally substituted with one or more, the same or different, $R^{10}$ or $R^{15}$;

$R^{10}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{10}$ is optionally substituted with one or more, the same or different, $R^{11}$ or $R^{15}$;

$R^{11}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{11}$ is optionally substituted with one or more, the same or different, $R^{12}$ or $R^{15}$;

$R^{12}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{12}$ is optionally substituted with one or more, the same or different, $R^{13}$ or $R^{15}$;

$R^{13}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{13}$ is optionally substituted with one or more, the same or different, $R^{14}$ or $R^{15}$;

$R^{14}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{14}$ is optionally substituted with one or more, the same or different, $R^{15}$;

$R^{15}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

$R^2$ is selected from alkyl, alkenyl, alkanoyl, cyano, carboxy, alkylamino, dialkylamino, carbocyclyl, aryl, and heterocyclyl wherein $R^2$ is optionally substituted with one or more, the same or different, $R^{20}$ or $R^{25}$;

$R^{20}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{20}$ is optionally substituted with one or more, the same or different, $R^{21}$ or $R^{25}$;

$R^{21}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{21}$ is optionally substituted with one or more, the same or different, $R^{22}$ or $R^{25}$;

$R^{22}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{22}$ is optionally substituted with one or more, the same or different, $R^{23}$ or $R^{25}$;

$R^{23}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{23}$ is optionally substituted with one or more, the same or different, $R^{24}$ or $R^{25}$;

$R^{24}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{24}$ is optionally substituted with one or more, the same or different, $R^{25}$;

$R^{25}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

$R^3$ is selected from alkyl, alkenyl, alkanoyl, cyano, carbocyclyl, aryl, and heterocyclyl wherein $R^3$ is optionally substituted with one or more, the same or different, $R^{30}$ or $R^{31}$;

$R^{30}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{30}$ is optionally substituted with one or more, the same or different, $R^{31}$; and $R^{31}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

In certain embodiments, the disclosure relates to methods of forming a ketone comprising mixing
a) a compound comprising a carboxylic acid,
b) a trialkylphosphite or other phosphorus containing reagent,
c) an carbon nucleophile or boronic acid,
d) a catalyst disclosed herein, and
e) copper under conditions such that a ketone is formed.

In certain embodiments, the disclosure relates to mixing a carbon nucleophile under conditions such that a ketone is formed. In further embodiments, the nucleophile is an alkyl, aryl, or heteroaryl optionally substituted from an alkyl boronic acid ester or an alkyl, aryl, or heteroaryl optionally substituted stannane which react via a copper catalyzed reaction with boronic acids (esters) or stannanes.

In certain embodiments, the boronic acid has the following formula:

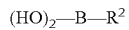

wherein,
$R^2$ is selected from alkyl, alkenyl, alkanoyl, carboxy, carbocyclyl, aryl, and heterocyclyl wherein $R^2$ is optionally substituted with one or more, the same or different, $R^{20}$ or $R^{25}$;

$R^{20}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{20}$ is optionally substituted with one or more, the same or different, $R^{21}$ or $R^{25}$;

$R^{21}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{21}$ is optionally substituted with one or more, the same or different, $R^{22}$ or $R^{25}$;

$R^{22}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{22}$ is optionally substituted with one or more, the same or different, $R^{23}$ or $R^{25}$;

$R^{23}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{23}$ is optionally substituted with one or more, the same or different, $R^{24}$ or $R^{25}$;

$R^{24}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{24}$ is optionally substituted with one or more, the same or different, $R^{25}$;

$R^{25}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

In certain embodiments, the ketone has the formula

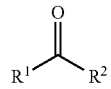

wherein,
$R^1$ is selected from alkyl, alkenyl, alkanoyl, carboxy, carbocyclyl, aryl, and heterocyclyl wherein $R^1$ is optionally substituted with one or more, the same or different, $R^{10}$ or $R^{15}$;

$R^{10}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{10}$ is optionally substituted with one or more, the same or different, $R^{11}$ or $R^{15}$;

$R^{11}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{11}$ is optionally substituted with one or more, the same or different, $R^{12}$ or $R^{15}$;

$R^{12}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{12}$ is optionally substituted with one or more, the same or different, $R^{13}$ or $R^{15}$;

$R^{13}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{13}$ is optionally substituted with one or more, the same or different, $R^{14}$ or $R^{15}$;

$R^{14}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{14}$ is optionally substituted with one or more, the same or different, $R^{15}$;

$R^{15}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

$R^2$ is selected from alkyl, alkenyl, alkanoyl, cyano, carboxy, alkylamino, dialkylamino, carbocyclyl, aryl, and heterocyclyl wherein $R^2$ is optionally substituted with one or more, the same or different, $R^{20}$ or $R^{25}$;

$R^{20}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{20}$ is optionally substituted with one or more, the same or different, $R^{21}$ or $R^{25}$;

$R^{21}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{21}$ is optionally substituted with one or more, the same or different, $R^{22}$ or $R^{25}$;

$R^{22}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{22}$ is optionally substituted with one or more, the same or different, $R^{23}$ or $R^{25}$;

$R^{23}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{23}$ is optionally substituted with one or more, the same or different, $R^{24}$ or $R^{25}$;

$R^{24}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{24}$ is optionally substituted with one or more, the same or different, $R^{25}$; and $R^{25}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

In certain embodiments, the disclosure relates to method of forming a carbon-carbon bond comprising mixing a trisubstituted phosphite; a sulfur, amide heterocycle; and silylating agent in a solvent followed by adding a compound comprising an hydroxyalkyl optionally substituted with one or more, the same or different, substituent under conditions such that a thiol intermediate is formed and mixing the thiol intermediate with copper, a carbon nucleophile and optionally another metal under conditions such that a carbon-carbon bond is formed between the carbon of the hydroxyl alkyl and the carbon nucleophile.

In certain embodiments the disclosure relates to method of forming a carbon-carbon bond comprising mixing a) an hydroxylalkyl, b) a trisubstituted phosphite; c) a catalytic heterocycle; d) a carbon nucleophile and e) $Z(R^9)_3$ wherein Z is selected from P, As, Sb, Bi and $R^9$ is individually at each occurrence alkyl, aryl, or heteroaryl optionally substituted with one or more, the same or different, substitutents under conditions such that carbon to carbon bond is formed between the nucleophile and the alkyl. In certain embodiments, the carbon nucleophile is cardioxide or carbon monoxide.

In any of the embodiments disclosed herein a copper catalyst may be used in combination with other catalysts such as palladium.

Examples

The Desulfitative Redox Catalysts

Figure 1B:
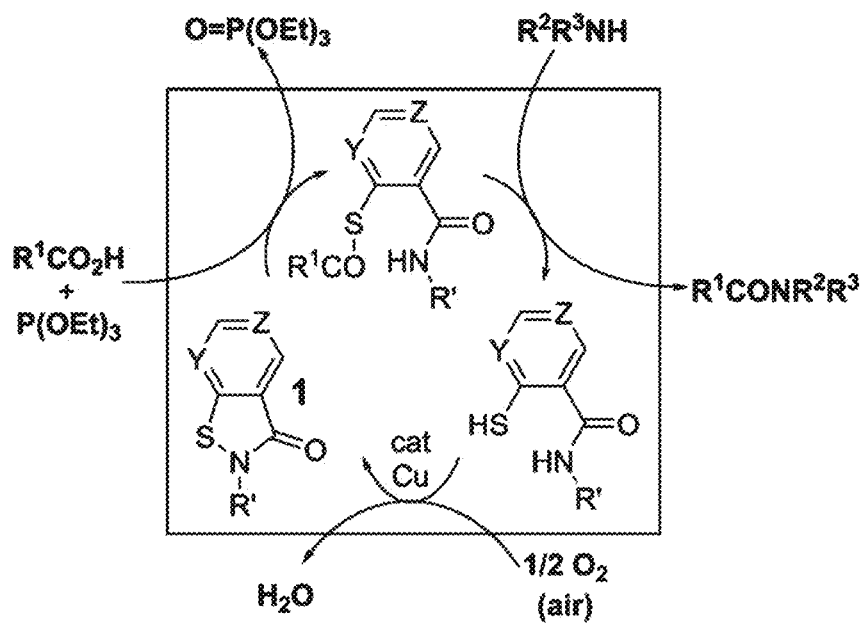
FIG. 1B illustrates amide bond formation. Carboxylic acids and amine/amino acid reactants can be converted to amides and peptides at neutral pH within 5-36 h at 50° C. using catalytic quantities of a redox-active benzoisothiazolone and a copper complex. These catalytic "oxidation-reduction condensation" reactions are carried out open to dry air using O₂ as the terminal oxidant and a slight excess of triethyl phosphite as the reductant. Triethyl phosphate is the easily removed byproduct. These simple-to-run catalytic reactions provide practical and economical procedures for the acylative construction of C—N bonds.
Figure 1C:
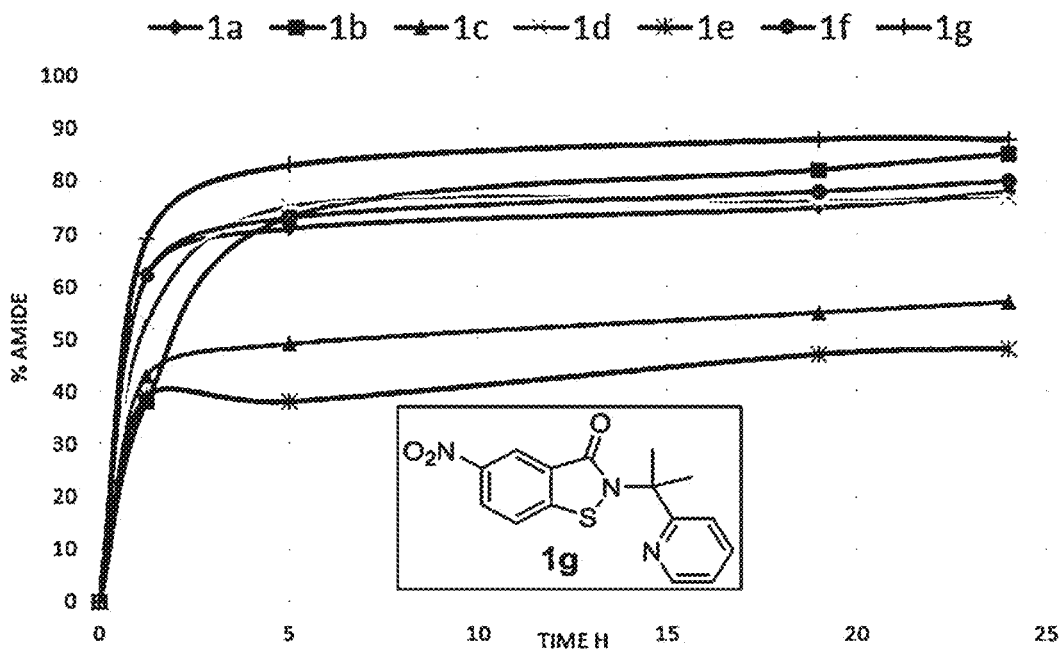
FIG. 1C shows a brief comparative survey of the different redox organocatalytic BITs listed at the bottom of FIG. 1B (1a, 1b, 1c, 1d, 1e, 1f, and 1g) was carried out. The formation of (p-tolyl)CONHBn from 1.0 equiv of p-toluic acid, 1.2 equiv of benzylamine, and 1.5 equiv of (EtO)3P was investigated using 10 mol % CuI₂(NMI)₄ and 20 mol % BIT in MeCN at 50° C. (dry-air atmosphere and activated 4 Å molecular sieves). These experiments revealed modest differences in the initial reaction rates as the nature of the aromatic ring and the N substituent were varied. Among the BITs studied to date, BIT 1g was a top performer, providing an improved reaction rate and conversion to amide.
Figure 3:
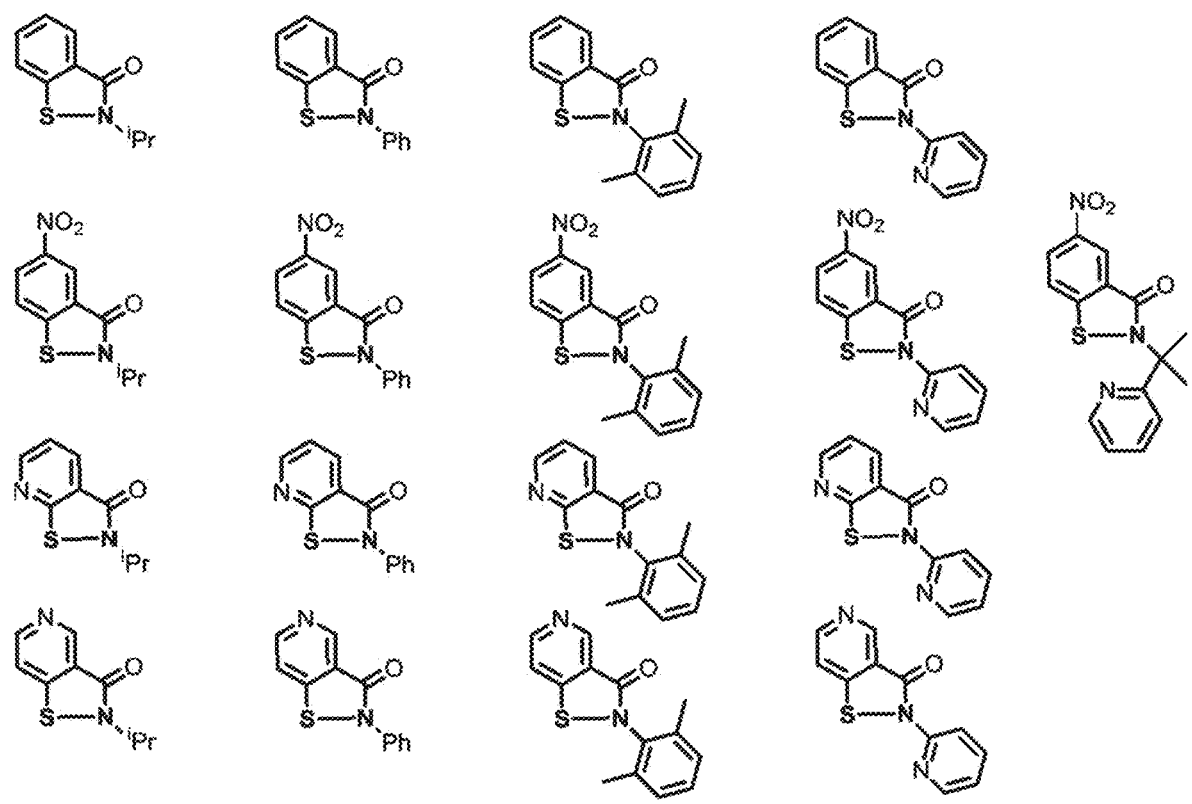
FIG. 3 sulfur-based heterocyclic catalysts, the benzoisothiazolones.
Figure 5:
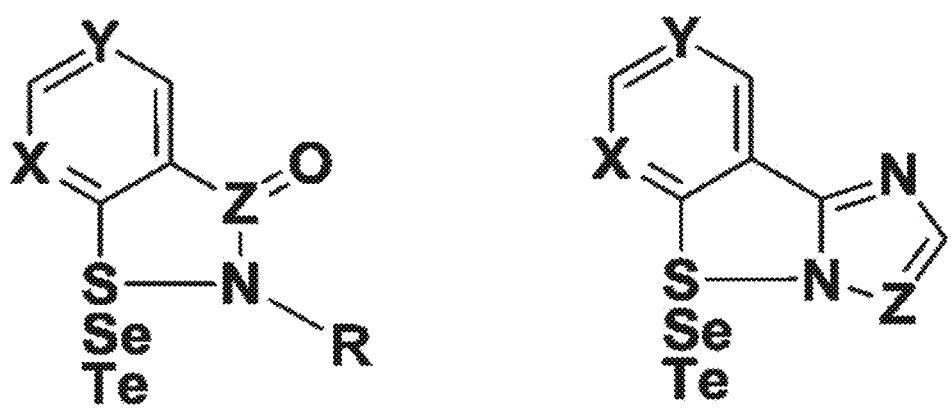
FIG. 5 illustrates additional heterocyclic catalysis of this disclosure. X and Y may be CH, N, $CNO_2$, as well as other electronic donating (e.g., $NR_2$, NHR, or OR) and electron withdrawing substitutents (e.g., a carbon oxide, sulfur oxide, phosphorus oxide, or nitrogen oxide, $NO_2$, (C=O)R, (C=O)NHR, (C=O)OR, (C=O)SR, $SO_3H$, $SO_2R$, (S=O)R, $PO_2R$, (P=O)$R_2$, (P=O)(OR)$_2$).
Figure 6:
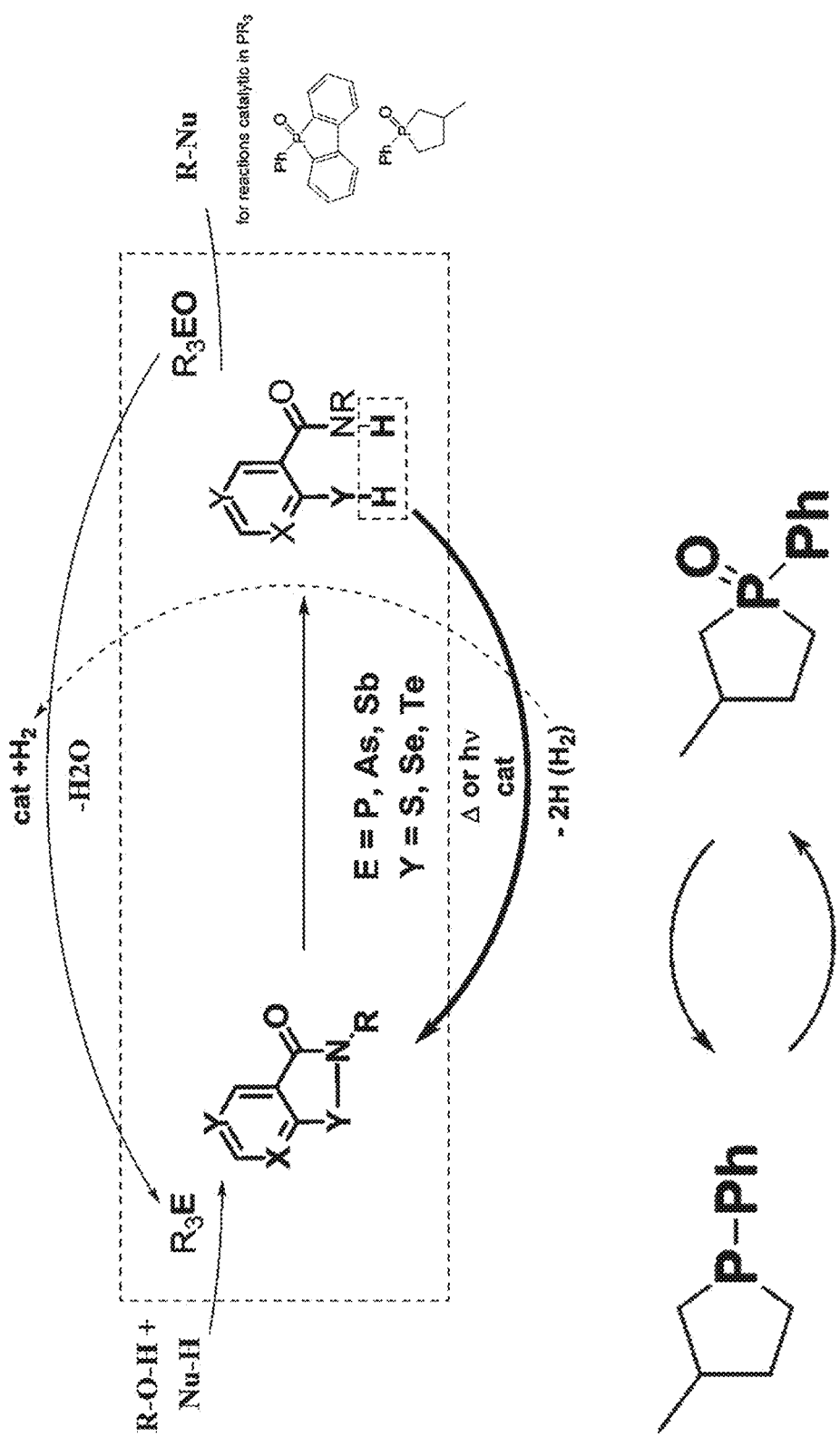
FIG. 6 illustrates alternative reagents or conditions for a fully catalytic oxidation-reduction system for dehydrative coupling making use of and $PR_3$ oxidation through phosphine oxides possessing strained five membered or smaller ring sizes to facilitate facile reduction of the phosphine oxide back to the phosphine in a catalytic protocol. See O'Brien et al., Chem Eur J, 2013, 19 5854.
Figure 7:
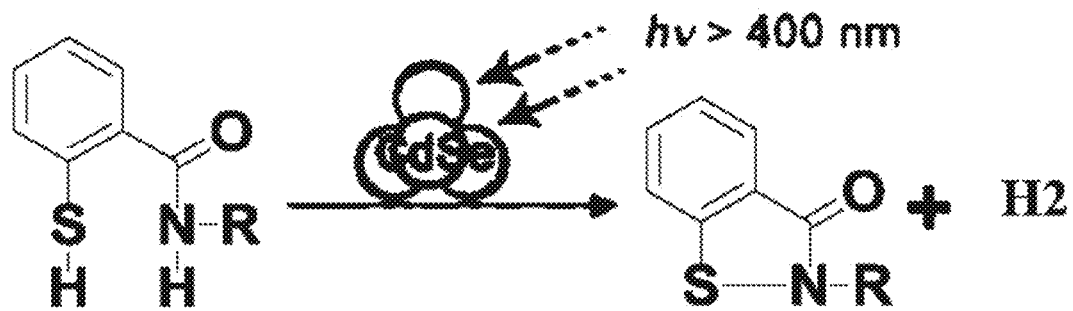
FIG. 7 illustrates light induced oxidation of using CdSe nanoparticles using conditions as reported in Li et al. Angew Chem Int Ed Engl. 2014 Feb. 17; 53(8):2085-9. Visible-light irradiation of CdSe QDs was found to result in quantitative coupling of a variety of thiols to give disulfides and $H_2$ without the need for sacrificial reagents or external oxidants. The addition of small amounts of nickel(II) salts improved the efficiency and conversion.
Figure 8:
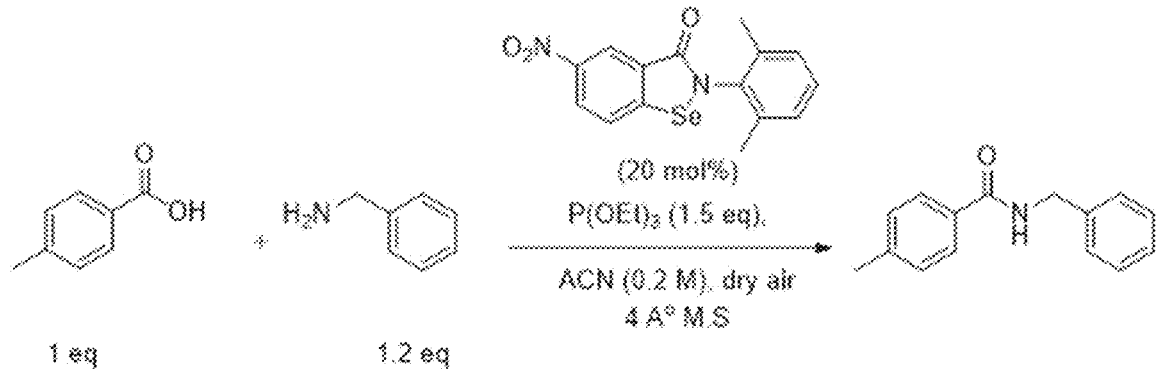
FIG. 8 illustrates additional embodiments of the disclosure the significant increase in the rate of reaction when the sulfur-based catalysts are replaced with their selenium-based analogs. 2-(2,6-dimethylphenyl)-5-nitrobenzo [d][1,2] selenazol-3(2H)-one was prepared following the procedure in Org. Lett., 2010, 12, 5394-5397.
Figure 9:
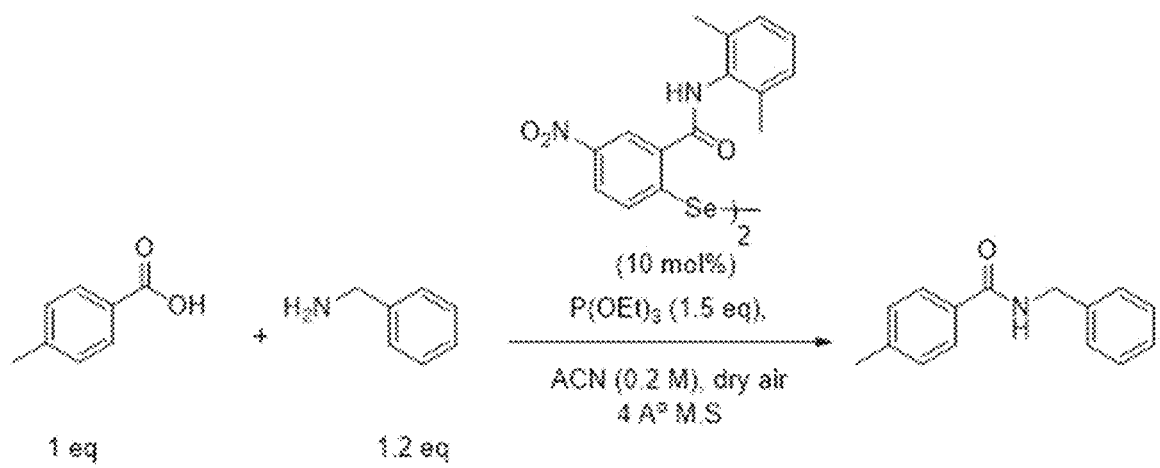
FIG. 9 illustrates additional embodiments of the disclosure wherein the diselenide catalyst related to the selenazolone catalyst of FIG. 8 is utilized and suggests that either selenazolone or the corresponding diselenide can be used as an effective catalyst under the conditions of the reaction.

The desulfitative redox catalysts of this disclosure cover any molecular system bearing a sulfur to nitrogen bond (a sulfenamide) that is generated either in an intramolecular or an intramolecular fashion in the presence of a catalyst and either air (O2) or an oxidant (FIG. 1 and). A representative series of "intramolecular" desulfitative redox catalysts are shown in (FIG. 3). Each of the desulfitative redox catalysts possesses heteroatom O- and N-control points at which either protic or Lewis acids can potentially influence the reactivity of the individual steps of the desulfitative redox cycle: (1) thioester C—S bond formation, and (2) subsequent desulfitative C—N bond formation with simultaneous oxidative regeneration of the desulfitative redox catalysts. Electronic tuning of reactivity is also feasible by variation of substituents Z=CH, $CNO_2$, and N at the positions of substitution indicated in FIG. 5.

Figure 2:
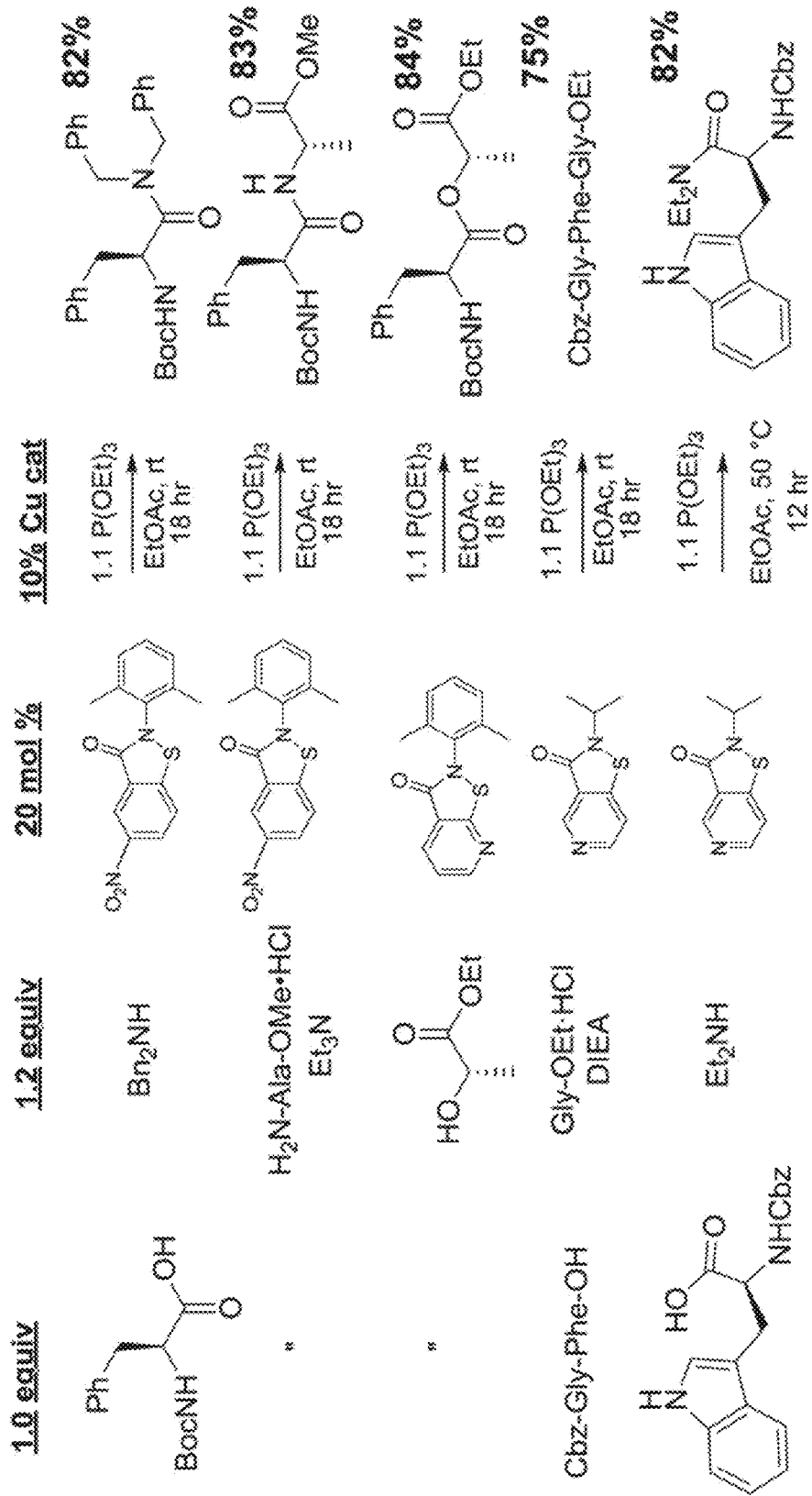
FIG. 2 illustrates additional embodiments of the disclosure using sulfur-based heterocyclic catalysts.

The direct conversion of carboxylic acids and benzoisothiazolones (FIGS. 1 and 2) into the corresponding thioesters can be done by a Mukaiyama-like redox dehydration using benzoisothiazolones, and a reactive triorganophosphine ($PPh_3$, $PBu_3$). This protocol was improved by replacing the triorganophosphine with the phosphite, $P(OMe)_3$. Using this phosphite avoids the use of the more reactive phosphines for the redox dehydration, and simplifies workup and purification because the $P(OMe)_3$ is transformed into easily removed, watersoluble trimethylphosphate. Surprisingly, the use of a phosphite, e.g., $P(OMe)_3$, in generating the thioester is not compromised by Arbuzov-like demethylation side reactions, a known problem in azodicarboxylate-based Mitsunobu reactions. See Véliz et al. Mitsunobu reactions of nucleoside analogs using triisopropyl phosphite-DIAD. Tetrahedron Lett. 2006, 47, 3153-3156. Interference from Arubzov like side-reactions with phosphite reagents may be the reason that phosphites have not yet been explored in generating thioesters. Also contemplated are heterocyclic phosphines that are five membered rings.

One can use open-to-air reaction of amines with thioesters, generated from a carboxylic acid, P(OMe)$_3$, and a desulfitative redox catalyst, to give amides that takes place coincident with aerobic regeneration. This represents an economical and practical "desulfitative redox catalytic route to amides directly from carboxylic acids, amines, air, and P(OMe)$_3$ under mild conditions.

Figure 10:
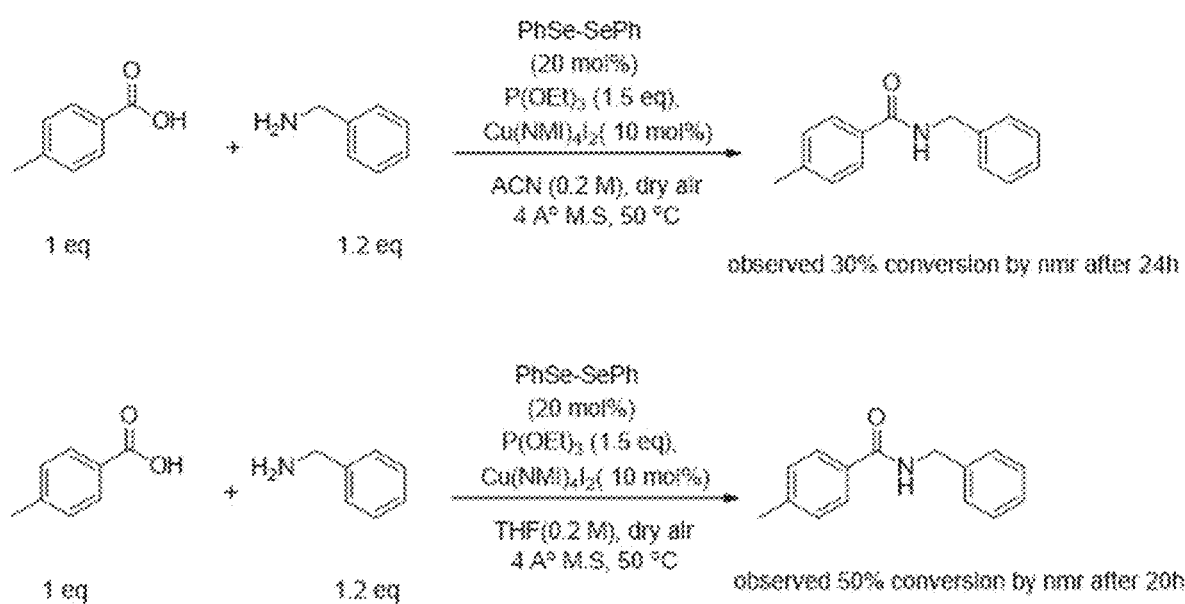
FIG. 10 illustrates additional embodiments of the disclosure.
Figure 11:
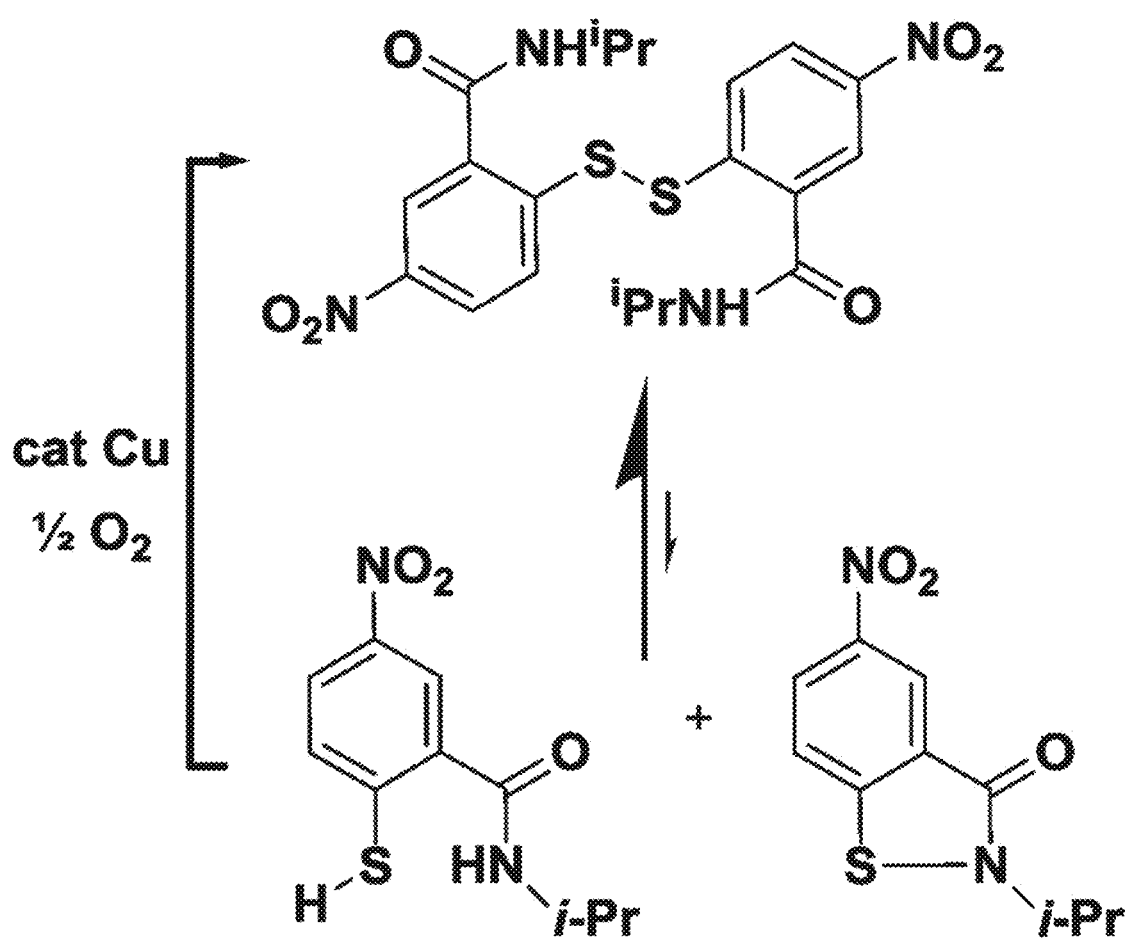
FIG. 11 illustrates different oxidation states of the catalysts of the disclosure. Both the disulfide and the calcolgen containing heterocycle can be active catalytic oxidants under reaction conditions.
Figure 12:
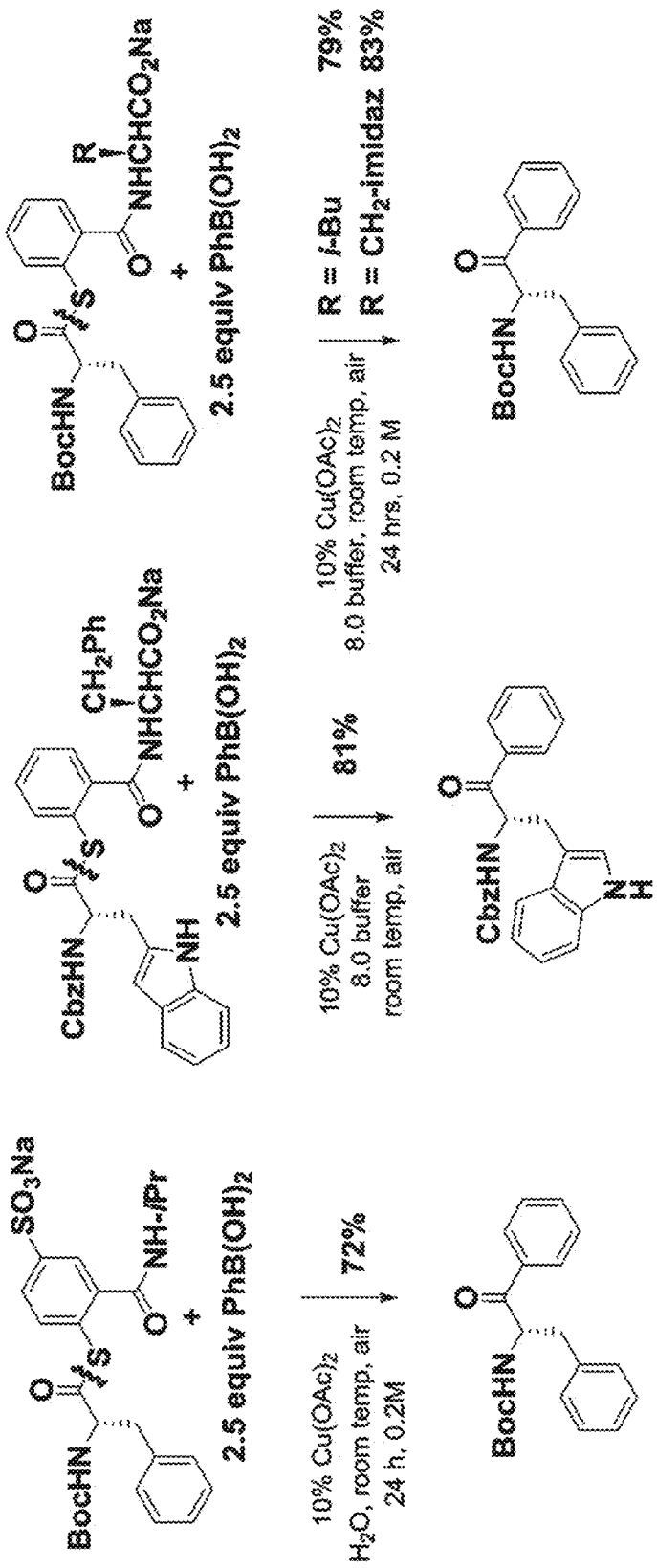
FIG. 12 illustrates additional embodiments of the disclosure.

Thioester generation and desulfitative amide/peptide bond formation, can be linked in one pot without isolation of intermediates (batch-mode recycle). It is desirable if both reaction steps can take place open to air under the same or similar conditions, thus allowing the desulfitative redox catalyst to be used catalytically rather than in a batch recycle mode. Solid-phase supported catayulic systems are useful in fully catalytic mode applications of the desulfitative redox catalysts. Attachment procedures can be pursued through the amide/sulfonamide R' group of 1 and 2, and through R" of 1-4 where Z═CSO2NHR" (Z in FIG. 10). See Testero & Mata, Prospect of Metal-Catalyzed C—C Forming Cross-Coupling Reactions in Modern Solid-Phase Organic Synthesis. J. Comb. Chem., 2008, 10, (4), 487-497.

The use of desulfitative redox catalysis for amide bond formation using desulfitative redox catalysts are illustrated in FIGS. 2, 4, 8, 9, and 10 and the schemes below.

Amide Bond Formation Reaction:

A 12 ml test tube was charged with a 4° A molecular sieves (300 mg) and activated in microwave oven for 3 min twice. Then, Acid (0.551 mmol), 4-Pyridyl BIT (0.110 mmol) and CuI$_2$(NMI)$_4$ (0.055 mmol) were added and diluted with dry Acetonitrile (2.75 mL, 0.2M, mc=5 ppm). Triethyl phosphite (0.716 mmol) was added to the reaction mixture at 55° C. and after 5 min was added amine (0.606 mmol) at 55° C. The reaction mixture was stirred for 24-48 h at 55° C. under the dry air balloon and filtered. The filtrate was purified by flash chromatography to obtain the pure amide.

Amide Bond Formation Using Selenazol-3-One Catalyst:

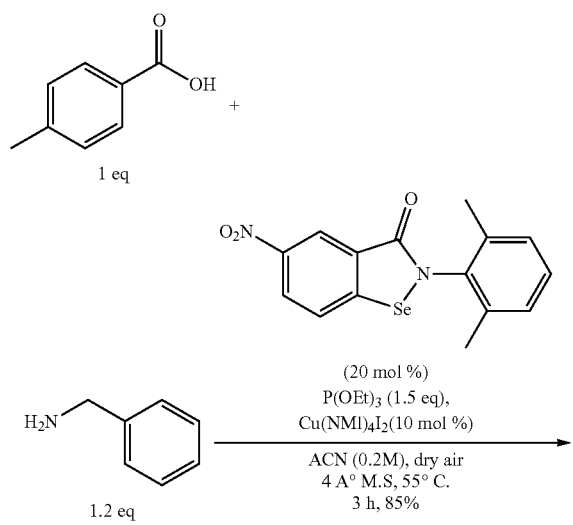

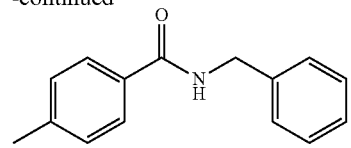

To a mixture of p-toluic acid (50 mg, 0.37 mmol), selenazol-3-one (26 mg, 0.074 mmol), CuI$_2$(NMI)$_4$ (24 mg, 0.037 mmol) and 4A° M.S (200 mg) in ACN (1.8 mL) was added triethyl phosphite (95 μl, 0.55 mmol) followed by benzylamine (48 μl, 0.44 mmol). The reaction mixture was heated to 55° C. under dry air. After completion (3 h) the reaction mixture was filtered, concentrated and subjected to flash column chromatography to get the amide (71 mg, 85% yield).

Amide Bond Formation Using Diselenide Catalyst:

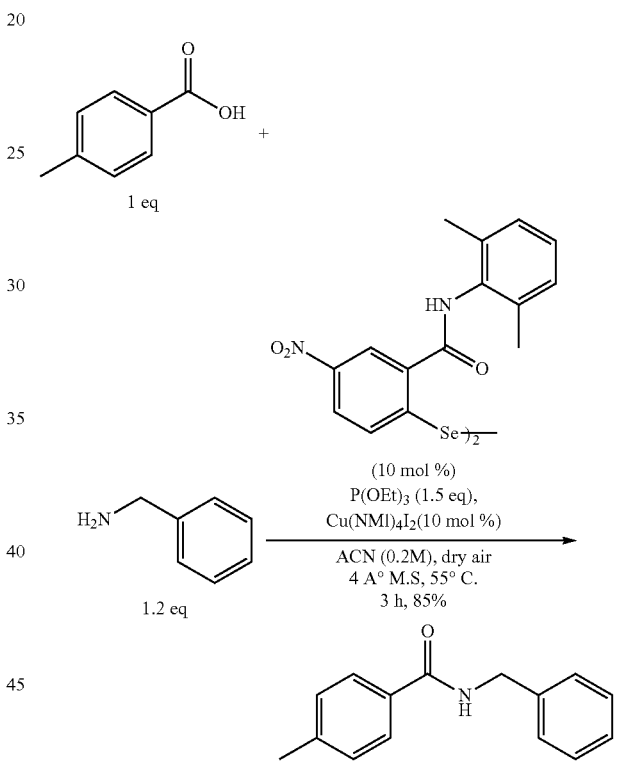

To a mixture of p-toluic acid (50 mg, 0.37 mmol), diselenide (26 mg, 0.037 mmol), CuI$_2$(NMI)$_4$ (24 mg, 0.037 mmol) and 4A° M.S (200 mg) in ACN (1.8 mL) was added triethyl phosphite (95 μl, 0.55 mmol) followed by benzylamine (48 μl, 0.44 mmol). The reaction mixture was heated to 55° C. under dry air. After completion (3 h) the reaction mixture was filtered, concentrated and subjected to flash column chromatography to get the amide (71 mg, 85% yield).

General Procedure for Preparation of Catalysts

Figure 13:
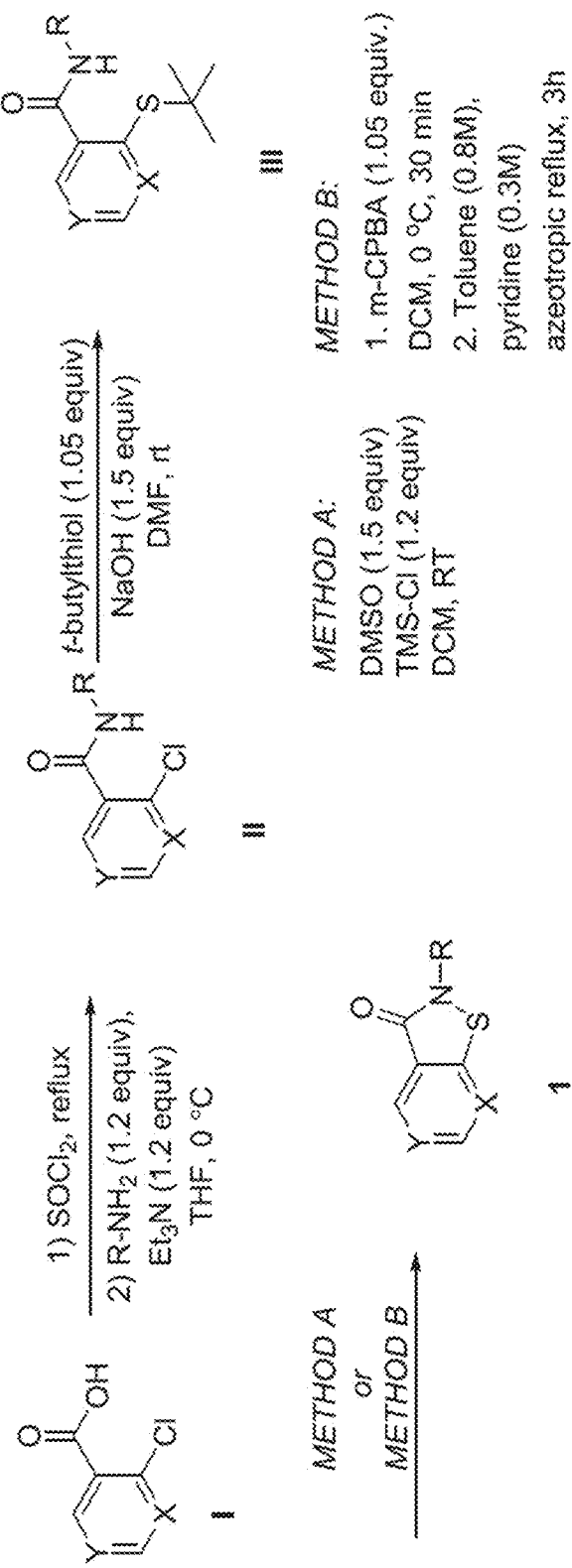
FIG. 13 illustrates methods of making catalysts disclosed herein.

The following procedures are illustrated in FIG. 13.

For synthesis of an amide, in a flame-dried round bottom flask, acid I (22.3 mmol) was added to thionyl chloride (15 mL, 223 mmol). The reaction was equipped with a reflux condenser and placed under an argon atmosphere and heated to reflux from one hour to overnight and then cooled to room temperature. Excess thionyl chloride was removed under vacuum. The resulting solid was taken up in dry THF (15 mL) and added dropwise to a solution of appropriate amine (26.8 mmol) and triethylamine (26.8 mmol) in THF (134 mL) at 0° C. After completion of the reaction as monitored by silica gel TLC (by a small portion of the reaction mixture was quenched with methanol), the reaction was concentrated to dryness. To the reaction mixture sat'd. NaHCO$_3$(50 mL) was added and extracted with CH2Cl2 (100 mL and 50 mL). The combined CH2Cl2 layers were washed with aqueous sat'd. NaCl (50 mL), dried over anhydrous Na2SO4 and concentrated under vacuum. The crude product was purified by either recrystallization from 1:1 water/EtOH or by SiO2 flash column chromatography eluting with ethyl acetate/hexanes.

For the synthesis of a thioether, In a flame-dried flask flushed with argon, IIa-i (list grams used, 20.2 mmol) and t-butyl thiol (2.7 mL, 24.2 mmol) were taken up in DMF (15 mL) and to this was added sodium hydroxide (900 mg, 22.2 mmol) at 25° C. The reaction was stirred at 25° C. for 3-18 hours. The completion of the reaction was monitored by TLC (SiO2, EtOAc/hexanes mixtures) after which the reaction mixture was poured into either 150 mL of a 5% aqueous HCl solution or 150 mL of water and stirred for 3 h at room temp. The resulting precipitate was filtered or extracted with CH2Cl2. The solid was collected and recrystallized from a refluxing mixture of ethanol and water (1:1) to provide IIIa-i as a solid.

METHOD A:

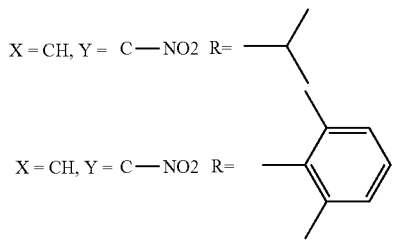

METHOD B:

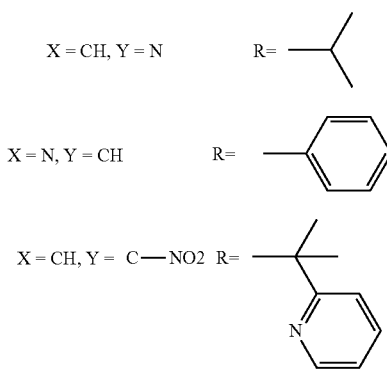

Method A:

In a flamed-dried round bottom flask filled with argon, t-butylthioethers IIIa-b (18.9 mmol) and DMSO (2.0 mL, 28.3 mmol) were combined and taken up in 50 mL of CH2Cl2. TMSCl (3.1 mL, 24.6 mmol) was slowly added to this mixture at 25° C. and the reaction was stirred for 8 hours. Upon completion of the reaction as judged by TLC on silica gel plates (EtOAc:hexanes), 100 mL of hexanes was added to the reaction and the precipitated product was filtered. The crude product was recrystallized from ethanol to provide the pure products 1a-b.

Method B:

In a flame-dried flask, t-butylthioether IIIc, IIIe or IIIg (5 mmol) was taken up in 50 mL of CH2Cl2. The mixture was cooled to 0° C., and mCPBA (5.5 mmol) was added in portions. The mixture was stirred at 0° C. for 30 min. Completion of the reaction was monitored by TLC (SiO2, EtOAc/hexanes mixtures) after which the reaction was quenched with 50 mL of sat. NaHCO$_3$. The layers were separated and the aqueous layer was extracted twice with CH2Cl2 (50 mL). The combined organic layers were washed with sat'd aqueous Na2S2O3 solution, dried over anhydrous MgSO4, filtered and concentrated. The residue of the crude sulfoxide was dissolved in toluene (100 mL) and pyridine (10 mL) and then heated to reflux with azeotropic removal of water. After 3 hours, the reaction was cooled to room temperature and concentrated to dryness. The residue was purified by silica gel chromatography (EtOAc:hexanes).

2-Phenylbenzo[d]isothiazol-3(2H)-one

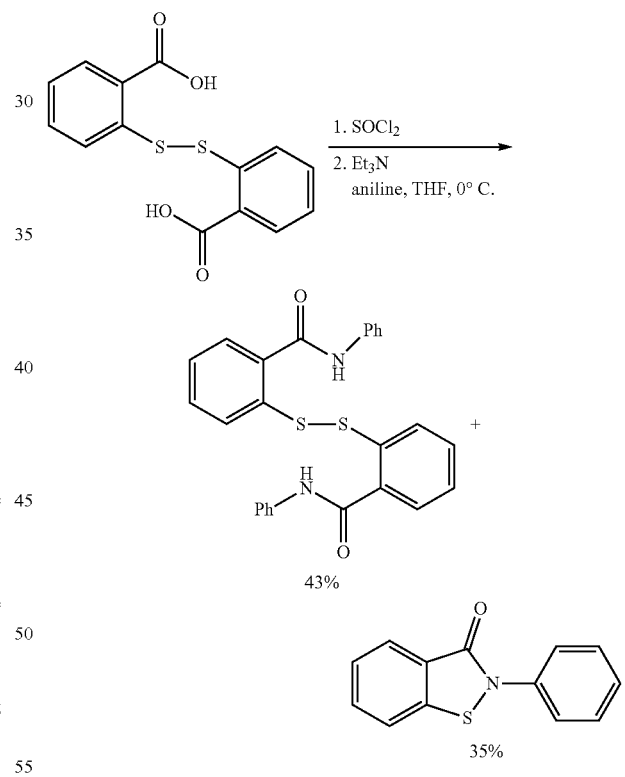

In a flame-dried round bottom flask, 2,2'-disulfanediyldibenzoic acid (5 g, 16.3 mmol) was added to 12.3 mL of thionyl chloride. The reaction was heated to reflux and stirred overnight. Excess thionyl chloride was removed under vacuum. The resulting solid was taken up in 10 mL of dry THF and added dropwise to a solution of aniline (2.85 g, 30.8 mmol) and triethylamine (4.27 mL, 30.8 mmol) in 80 mL of THF at 0° C. After completion of the reaction as monitored by SiO2 TLC (by treating a small portion of the reaction mixture with methanol), the reaction was concentrated to dryness. The solid residue was triturated with sat'd.

NaHCO$_3$ (50 mL), filtered and washed with CH2Cl2 (100 mL) to leave behind 2,2'-disulfanediylbis(N-phenylbenzamide) as a white solid (2.89 g, 43% yield). The NaHCO$_3$/CH2Cl2 filtrate was separated and the aqueous layer extracted with CH2Cl2 (100 mL and 50 mL). The combined CH2Cl2 layers were back-washed with aqueous sat'd. NaCl (50 mL), dried over anhydrous Na2SO4, filtered, and concentrated in vacuum. The crude product was purified by SiO2 column chromatography using ethyl acetate and hexanes as an eluent to provide 2-phenylbenzo[d]isothiazol-3(2H)-one (1d) as an off-white solid (2.25 g 34% yield).

Screening of Cu-Ligand Source

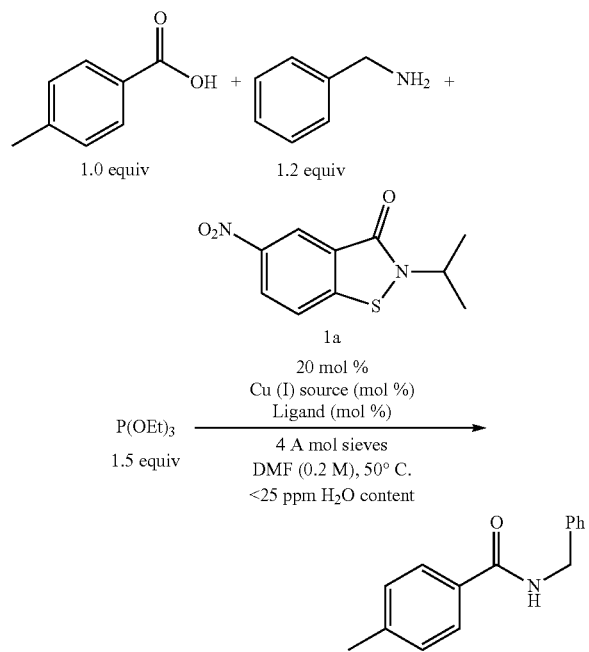

A 12 mL test tube was charged with a 4 Å molecular sieves (275 mg) that were activated in a microwave oven for 3 min, twice, and kept under reduced pressure for 5 min. Then, p-toluic acid (0.551 mmol), BIT 1a (0.110 mmol), Cu(I) source (10%) and ligand (mol % in Table 1, below) were added followed by dry DMF (2.75 mL, 0.2M, moisture content <25 ppm). Triethylphosphite (0.716 mmol) was added to the reaction mixture at the temperature in the Table 1 and after 5 min the benzyl amine (0.606 mmol) was added. The reaction mixture was stirred for 48 h at the indicated temperature under a dry air atmosphere (balloon). The reaction mixture was filtered, washed with CH2Cl2 (25 mL) and the organic layer was washed with water. The separated organic layer was dried over anhydrous MgSO4, concentrated and purified by flash chromatography (SiO2, eluted with 10% EtOAc in hexanes to obtain the pure p-tolylbenzylamide.

TABLE 1

| | CU(I) source (mol %) | ligand (mol %) | time h | temperature | yield %$^a$ |
|---|---|---|---|---|---|
| 1. | CuI (10) | bpy (10) | 48 | 25° C. | 16 |
| 2. | CuI (10) | bpy (10) | 48 | 50° C. | 22 |
| 3. | CuI (10) | DAF$^9$ (10) | 48 | 50° C. | 41 |
| 4. | CuI (10) | NMI (20) | 48 | 50° C. | 45 |
| 5. | CuCl (10) | NMI (20) | 48 | 50° C. | 28 |

TABLE 1-continued

| | CU(I) source (mol %) | ligand (mol %) | time h | temperature | yield %$^a$ |
|---|---|---|---|---|---|
| 6. | CuBr (10) | NMI (20) | 48 | 50° C. | 32 |
| 7. | Cu(CH$_3$CN)$_4$PF$_6$ (10) | NMI (20) | 48 | 50° C. | 21 |
| 8. | Cu(I)MeSalicylate (10) | NMI (20) | 48 | 50° C. | 24 |
| 9. | CuI (10) | bpy (10) NMI (20) | 48 | 50° C. | 33 | bpy: 2,2'-Bipyridine;
NMI: N-Methylimidazole;
DAF: 4,5-Diazafluoren-9-one
$^a$isolated yield.

CuI$_2$(NMI)$_4$ Complex

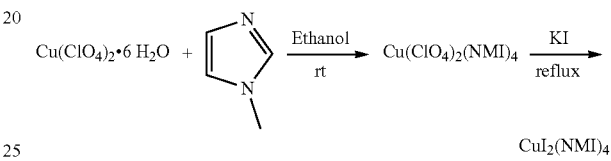

To copper (II) perchlorate. 6H$_2$O (10 g, 27.0 mmol) dissolved in ethanol (400 mL) was added 1-methylimidazole (10.76 mL, 135 mmol) at 25° C. and stirred for 30 min. Then, potassium iodide (13.44 g, 81 mmol) was added to the above reaction mixture which was heated to reflux temperature. After 3 h at reflux temperature, the reaction mixture was filtered under hot conditions and washed with hot ethanol (50 mL). The filtrate was allowed cool to 25° C. with slow stirring, and then left overnight at 25° C. It was then filtered, washed with cold ethanol and diethyl ether to provide blue-green crystals (7.2 g). The molecular structure was determined by X-ray crystallography and bulk purity was determined by elemental analysis.

General Procedure for Amide Bond Formation

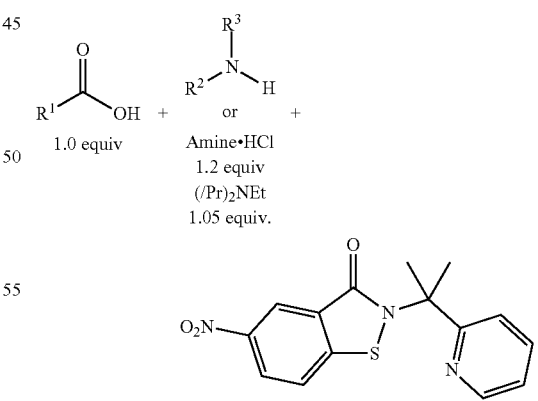

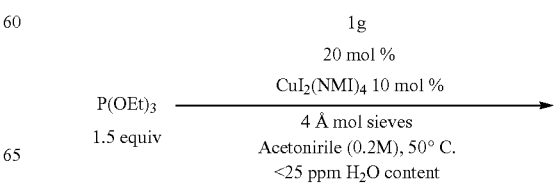

-continued

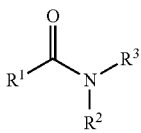

A 12 mL test tube was charged with a 4 Å molecular sieves (275 mg), activated in a microwave oven for 3 min twice and kept under reduced pressure for 5 min. Then, acid (0.551 mmol), BIT 1g (0.110 mmol) and CuI2(NMI)4 (0.055 mmol) were added and followed by dry acetonitrile (2.75 mL, 0.2M, moisture content <25 ppm). Triethyl phosphite (0.716 mmol) was added to the reaction mixture at 50° C. and after 5 min, was added amine (0.606 mmol) or amine HCl (0.606 mmol) with DIPEA (0.578 mmol) at 50° C. The reaction mixture was stirred for 10-36 h at 50° C. under a dry air atmosphere (balloon). The complete conversion of acid was monitored by TLC, the reaction mixture was filtered and washed the molecular sieves with CH2Cl2 thoroughly. The combined filtrate was concentrated under reduced pressure and the crude product was purified by flash column chromatography (silica gel with ethyl acetate in hexanes) to obtain the pure amide product.

Catalytic Redox Dehydration Reactions for Amide that Use Benzoisoselenazolones or Diselenides at Room Temperature without Cocatalytic Cu Benzoisothiazolones and Cu complexes are useful as co-catalysts at 50° C. Benzoisoselenazolones and Cu complexes are useful as co-catalysts at near room temperature for catalytic redox dehydration. Catalytic redox dehydration reactions for amide preparation can be accomplished using benzoisoselenazolones or diselenides at room temperature without co-catalytic Cu.

Benzoisoselenazolones shown in FIG. 14 were prepared by standard synthetic procedures. See, e.g., Bijan et al. Eur J Med Chem. 2012, 48:143-52. When paired with triethylphosphite as a stoichiometric reductant and $O_2$ in air as the terminal oxidant, a number of the benzoisoselenazolones were effective redox dehydration catalysts for amidation at 5-10% loadings at 30° C. in MeCN under dry air. For comparative studies, the organocatalysts were used to generate N-benzyl-p-toluamide from 1.2 equiv toluic acid, 1.2 equiv benzylamine, 1.5 equiv triethylphosphite, 10 mol % $CuI_2(NMI)_4$, 0.2 M in MeCN at 30° C. with 4 Å mol sieves under dry air. Paralleling observations with the benzoisothiazolones, the N-alkyl benzoisoselenazolones are generally more robust catalysts than those bearing N-aryl substituents. Furthermore, catalytic efficiencies increased when electron-withdrawing substituents were placed para to the selenium on the benzoisoselenazolone aromatic ring (comparing 2f, 2g and 2h). Of the N-alkyl benzoisoselenazolones studied, two (2g and 2i) stood apart as significantly faster and more robust than the others. Both of these catalysts bear an activating nitro substituent para to the Se on the aromatic ring. Both selenium catalysts possess a basic N-ligand on the heterocycle pendant positioned 3-atoms removed from the amidic N of the benzoisoselenazolone. In contrast to the earlier studied with benzoisothiazolones, the benzoisoselenazolones 2g and 2i delivered the target amide in excellent yields within 6 hr in MeCN at only 5% loadings between room temperature and 30° C.

Benzoisothiazolone catalysts typically require the presence of co-catalytic Cu to aerobically regenerate themselves. Catalysts 2g and 2i where tested in the formation of N-benzyl-p-toluamide from 1.0 equiv toluic acid, 1.2 equiv benzylamine, and 1.5 equiv triethylphosphite at 0.2 M in MeCN at 30° C. with 4 Å mol sieves under dry air. Both 2g and 2i were highly effective organocatalysts in the absence of Cu.

Figure 16:
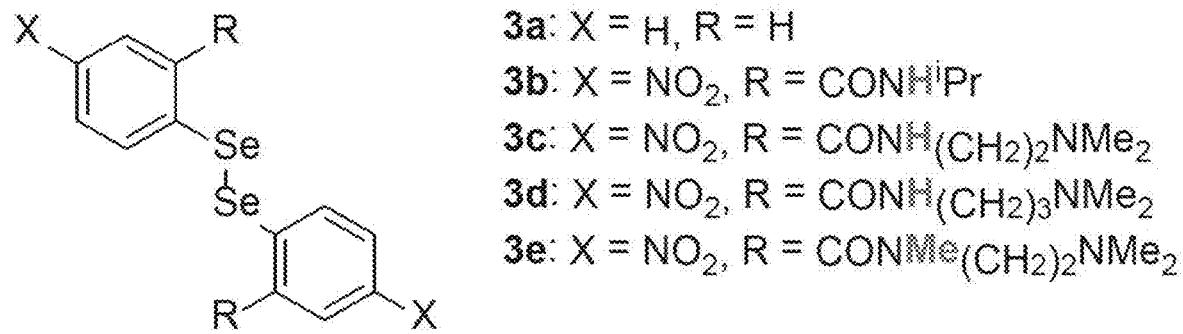
FIG. 16 illustrates diselenides.
Figure 17:
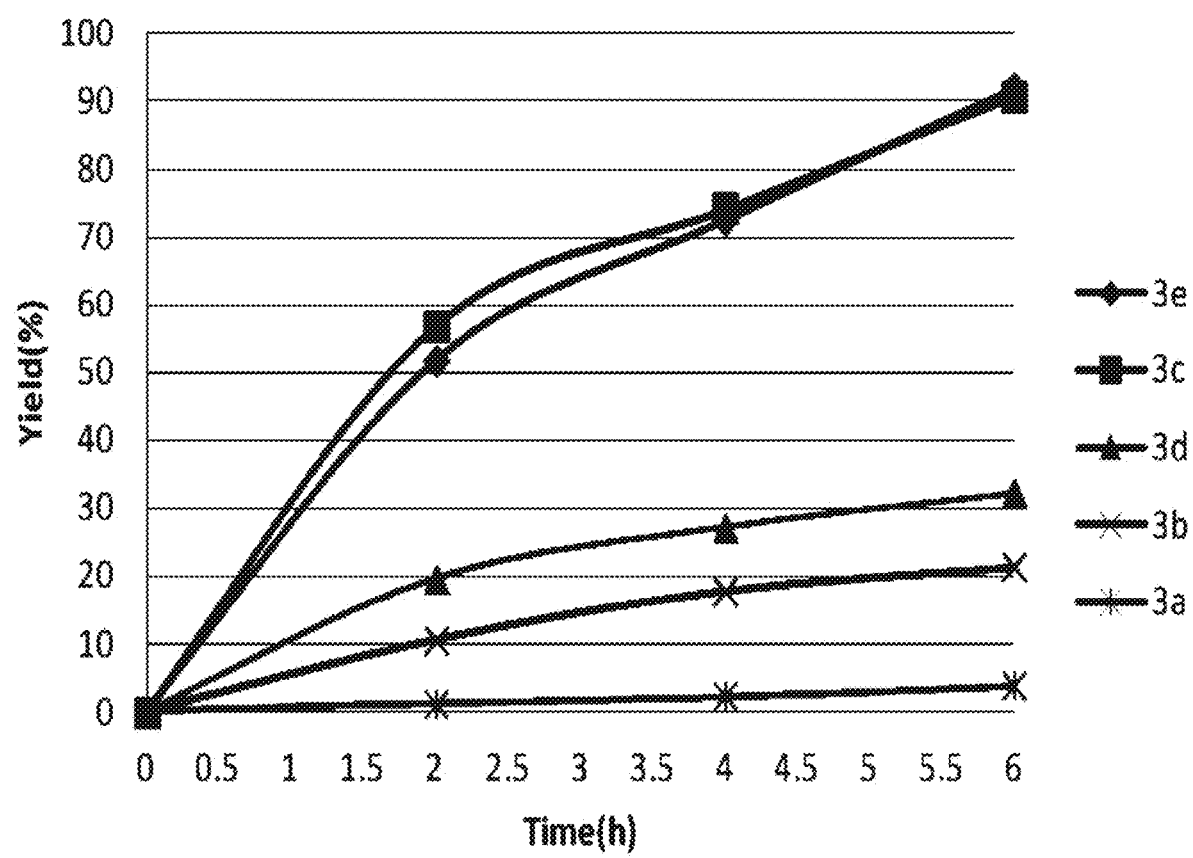
FIG. 17 shows catalytic data for diselenides illustrated in FIG. 16.

Diselenides 3a-e were prepared and studied as redox catalysts (FIG. 16). Both diselenides 3c (2° amide) and 3e (3° amide) at 2.5 mol % were highly effective organocatalysts for the aerobic redox dehydration of p-toluic acid and benzylamine to p-toluoyl N-benzylamide at 30° C. in MeCN (in the presence of 4 Å mol sieves) in the absence of a Cu catalyst. (FIG. 17). The Cu-free reactions catalyzed by both diselenides 3c and 3e were equally as fast and just as effective as the reactions catalyzed by the benzoisoselenazolones in the presence of the Cu cocatalysts. Diaryl diselenides 3a, b, and d were also effective to varying extents at redox dehydration, but they showed significantly lower activity as organocatalysts than 3c and 3e. The significant difference in reactivity of diselenides 3c and 3d that differ only in the distance of the —NMe2 unit from the amidic N-atom hints at an important role for intramolecular geometric factors in the catalysis.

Diselenide Catalyzed Aerobic Redox Dehydration Amidations

Figure 18:
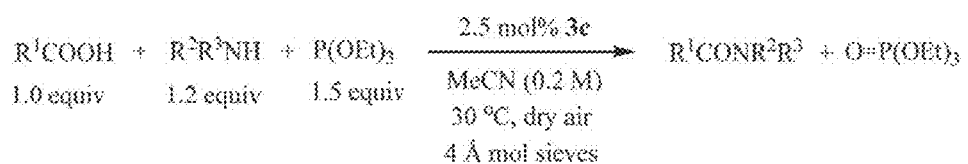
FIG. 18 shows catalytic data for compound 3c illustrated in FIG. 16 where an Amine-HCl/diisopropylethylamine was used. Triethyl phosphite and diisopropylethylamine were added at 0° C. No epimerization was observed by 1H NMR. b 1.0 equiv. of HOBt was used to minimize racemization. The reaction was allowed to warm slowly to 22° C. Negligible epimerization (98.5:1.5 er) was observed by HPLC.
Figure 19:
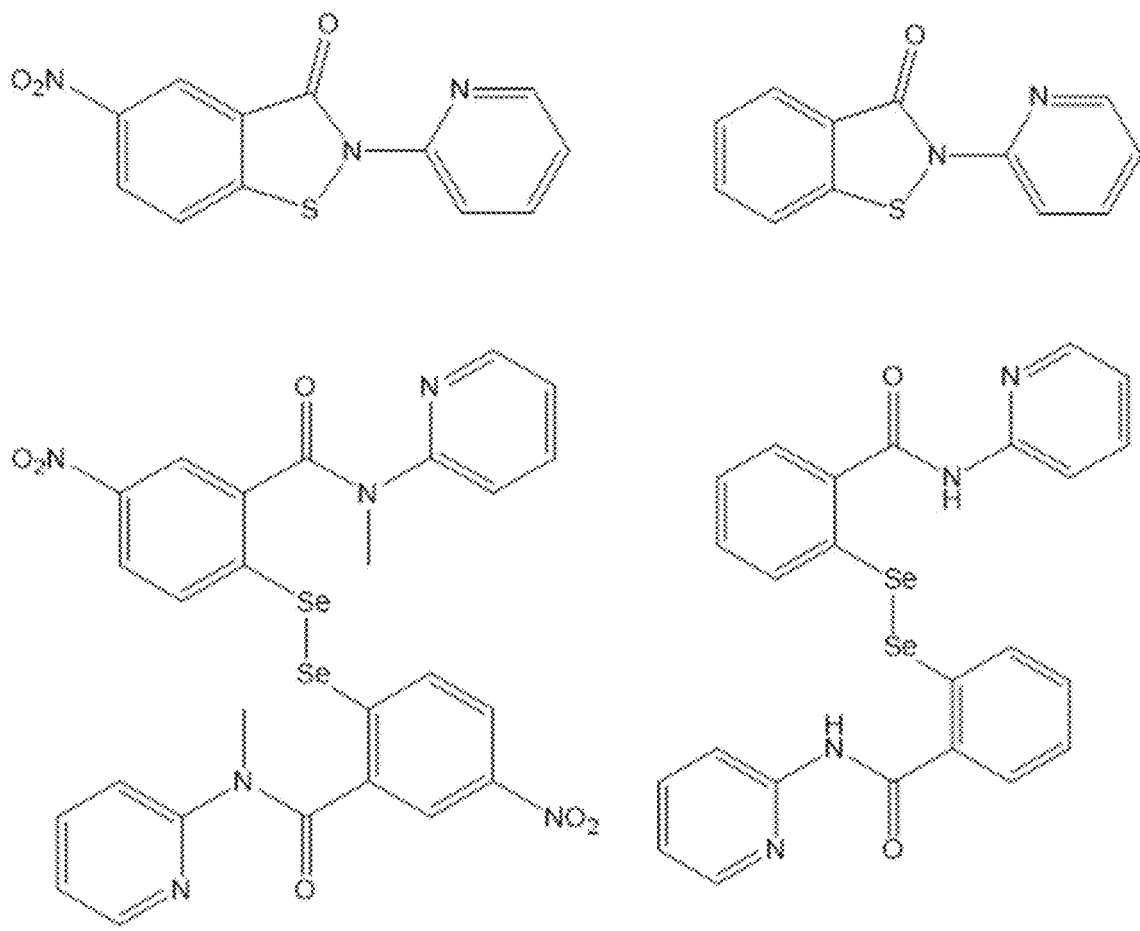
FIG. 19 illustrates embodiments of this disclosure.

At 2.5% catalyst loadings of 3c in MeCN at 30° C., the amides and peptides depicted in the Table shown in FIG. 18 were prepared from their corresponding carboxylic acid and amine partners by simply stirring open to a dry air balloon in the presence of 1.5 equiv of triethylphosphite. After complete conversion of carboxylic acid, the MeCN was removed under reduced pressure. The residue was taken up in dichloromethane, washed with aqueous 1.0 N HCl solution, dried over anhydrous $Na_2SO_4$ and concentrated to give the crude product. The crude product was purified by either silica column chromatography or recrystallization.

What we claim:
1. A method of catalyzing a coupling reaction comprising mixing
   a) a compound comprising a hydroxy group as a segment of a carboxylic acid group,
   b) a $PR_3$, wherein $PR_3$ is a trisubstituted phosphite, phosphine or a phosphorus containing five member heterocycle,
   c) an amine nucleophile, and
   d) a catalytic heterocycle which is 5-nitro-2-(2-(pyridin-2-yl) propan-2-yl)benzo[d]isothiazol-3(2H)-one:
   under conditions such that an amide compound is formed comprising the amine in place of the hydroxy group.
2. The method of claim 1, wherein mixing includes a $CuI_2(NMI)_4$.

* * * * *